United States Patent
Felsher et al.

(10) Patent No.: US 10,145,851 B2
(45) Date of Patent: Dec. 4, 2018

(54) DISCOVERY AND VALIDATION OF CANCER BIOMARKERS USING A PROTEIN ANALYSIS METHODOLOGY TO ANALYZE SPECIMENS

(71) Applicant: The Board of Trustees of the Leland Stanford Junior University, Stanford, CA (US)

(72) Inventors: Dean W. Felsher, San Mateo, CA (US); Alice Fan, Mountain View, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 121 days.

(21) Appl. No.: 15/004,601

(22) Filed: Jan. 22, 2016

(65) Prior Publication Data

US 2017/0205411 A1    Jul. 20, 2017

Related U.S. Application Data

(63) Continuation of application No. 12/757,745, filed on Apr. 9, 2010.

(Continued)

(51) Int. Cl.
*G01N 33/00* (2006.01)
*G01N 33/574* (2006.01)
*B82Y 15/00* (2011.01)

(52) U.S. Cl.
CPC .......... *G01N 33/5748* (2013.01); *B82Y 15/00* (2013.01); *G01N 33/57407* (2013.01);

(Continued)

(58) Field of Classification Search
None
See application file for complete search history.

(56) References Cited

U.S. PATENT DOCUMENTS 5,473,051 A    12/1995 Altieri et al.
6,245,754 B1    6/2001 Kozikowski et al.
(Continued)

FOREIGN PATENT DOCUMENTS

WO    2006/014680 A1    2/2006
WO    2009/058902 A2    5/2009

OTHER PUBLICATIONS

Deb-Basu; et al., "Measurement of Oncoproteins in Preclinical and Clinical Specimens Using a Nano-fluidic High Throughput Approach", 46th ASCB Annual Meeting (Dec. 2006), San Diego, Poster No. 2008A.

(Continued)

*Primary Examiner* — Melanie Yu Brown
*Assistant Examiner* — Richard Moerschell
(74) *Attorney, Agent, or Firm* — Pamela J. Sherwood; Bozicevic, Field & Francis LLP

(57) ABSTRACT

Methods are provided for the analysis, including the serial analysis, of very small samples of tissue. The methods utilize a nanofluidic proteomic immunoassay (NIA) to quantify total and low-abundance protein isoforms in a small amount of lysate. NIA detection accurately measure oncoprotein expression and activation in limited clinical specimens, including isoforms that differ in post-translational modifications, such as phosphorylation, and the like. The NIA detection method combines isoelectric protein focusing and antibody detection in a nanofluidic system.

16 Claims, 16 Drawing Sheets

Related U.S. Application Data

(60) Provisional application No. 61/168,493, filed on Apr. 10, 2009.

(52) U.S. Cl.
CPC ... *G01N 2333/82* (2013.01); *G01N 2333/912* (2013.01); *G01N 2570/00* (2013.01)

(56) References Cited

U.S. PATENT DOCUMENTS

| | | | |
|---|---|---|---|
| 7,846,676 B2 | 12/2010 | Yang et al. | |
| 7,935,308 B2 | 5/2011 | O'Neill et al. | |
| 7,935,479 B2 | 5/2011 | O'Neill et al. | |
| 7,935,489 B2 | 5/2011 | O'Neill et al. | |
| 2003/0086934 A1 | 5/2003 | Bolstein et al. | |
| 2003/0118589 A1 | 6/2003 | Sebti et al. | |
| 2005/0075287 A1 | 4/2005 | Van Gilst | |
| 2006/0292558 A1 | 12/2006 | O'Neill | |
| 2006/0292649 A1 | 12/2006 | Cahill et al. | |
| 2007/0059814 A1 | 3/2007 | Nakamura et al. | |
| 2009/0097022 A1 | 4/2009 | Shen et al. | |
| 2009/0208979 A1 | 8/2009 | Silver et al. | |
| 2010/0261224 A1 | 10/2010 | Felsher et al. | |
| 2011/0132761 A1 | 6/2011 | Yang et al. | |
| 2011/0195527 A1 | 8/2011 | O'Neill et al. | |

OTHER PUBLICATIONS

Deb-Basu; et al., "Measurement of oncoproteins in primary hematopoietic malignancies pre and post therapy using a nano-immunoassay system", 99th AACR Annual Meeting (Apr. 2008), Poster No. 5145.
Deb-Basu; et al., "Monitoring drug impact on signaling pathways from small samples of primary hematopoietic malignancies", 98th AACR Annual Meeting (Apr. 2007), Poster No. 2826.
Fan et al., "A nano-immunoassay system for monitoring changes in signaling upon oncogene inactivation in hematopoietic tumors", AACR-NCI-EORTC International Conference: Molecular Targets and Cancer Therapeutics Oct. 2007, San Francisco, Abstract C259.
Fan et al., "A nano-immunoassay system for monitoring targeted drug impact on signaling pathways from small samples of primary hematopoietic malignancies", First AACR Centennial Conference on Translational Cancer Medicine (Nov. 2007), Abstract C22.
Fan et al., "Monitoring changes in signaling proteins upon oncogene inactivation in hematopoietic tumors using a nanoimmunoassay system", 99th AACR Annual Meeting (Apr. 2008), San Diego, Abstract #3652.
Fan et al., "MYC Quantitation in Fine Needle Aspirate by "Firefly", a Novel Nanofluidic Protein Analysis System", AACR (2006), Abstract #3629.
Fan et al., "Nano-fluidic detection of oncoprotein signaling in clinical samples", 98th AACR Annual Meeting (Apr. 2007), Los Angeles, Abstract #2668.
Fan et al., "Nanoliter-scale Western-blot-like BCL-2 analysis of lymphoma fine needle aspirates", AACR (2006), Abstract #2499.
Felsher et al., "Spelling out cancer on the nanoscale: Nano-fluidic system roads onco-protein levels from tiny samples", 46th ASCB Annual Meeting, Press Book (Dec. 2006), San Diego, p. 16.
Voehringer et al., "A Nano-Immunoassay System for Monitoring Targeted Drug Impact on Signaling Pathways from Small Samples of Primary Hematopoietic Malignancies", AACR (2007), Singapore, Poster.
Voehringer et al., "A Nano-Immunoassay System for Monitoring Targeted Drug Impact on Signaling Pathways from Small Samples of Primary Hematopoietic Malignancies", Clinical Cancer Research 13.22 Supplement (2007), p. C22, American Association for Cancer Research, Philadelphia, PA.
Voehringer et al., "Single Antibody Determination of Phospho- and Non-phospho c-Myc in Small Samples with a New Blotless Nano Western System", 45th ASCB Annual Meeting (Dec. 2005), San Francisco, No. 2126, Abstract.
Voehringer et al., "Quantitative Analysis of Oncogene Products and Their Post-Translational Modifications", ASCB Meeting (2005), San Francisco, Poster No. 2126.
Robinson et al., "The protein tyrosine kinase family of the human genome", Oncogene, Nov. 20, 2000, pp. 5548-5557, 19(49), Macmillan Publishers, London, United Kingdom.
Parmar et al., "Role of the p38 mitogen-activated protein kinase pathway in the generation of the effects of imatinib mesylate (STI571) in BCR-ABL-expressing cells", J Biol Chem., Jun. 11, 2004, pp. 25345-25352, 279(24), American Society for Biochemistry and Molecular Biology, Inc., Rockville, MD.
Mann et al., Analysis of protein phosphorylation using mass spectrometry: deciphering the phosphoproteome, Trends Biotechnol., Jun. 2002, pp. 261-268, 20(6), Elsevier, Amsterdam, Netherlands.
Bhamidipati et al., "Protein Expression and Cell Signaling Quantified in Rare Cells", ISSCR (2008), Cell Biosciences poster.
Cole et al., "Proteomic analysis of colonic crypts from normal, multiple intestinal neoplasia and p53-null mice: A comparison with colonic polyps", Electrophoresis (2000), pp. 1772-1781, 21, Wiley, Hoboken, NJ.
Yu et al., "Both platelet-derived growth factor receptor (PDGFR)-alpha and PDGFR-beta promote murine fibroblast cell migration", Biochem Biophys Res Commun., Apr. 6, 2001, pp. 697-700, 282(3), Academic Press, Cambridge, MA.
Fan et al., "A quantitative PCR method to detect blood microRNAs associated with tumorigenesis in transgenic mice", Molecular Cancer (Sep. 30, 2008), pp. 1-8, 7:74, BioMed Central, London, United Kingdom.
Fan et al., "Nanofluidic proteomic assay for serial analysis of oncoprotein activation in clinical specimens", Nature Medicine (May 2009), pp. 566-571, 15(5), Macmillan Publishers, London, United Kingdom.
Fan et al., "Nanoscale Quantification of Phosphorylated and Unphosphorylated ERK and MEK Isoforms Differentiates Tumor and Non-tumor Clinical Specimens", AACR (2009), Leland Stanford Junior University poster.
Forozan et al., "Comparative Genomic Hybridization Analysis of 38 Breast Cancer Cell Lines: A Basis for Interpreting Complementary DNA Microarray Data", Cancer Research (Aug. 15, 2000), pp. 4519-4525, 60, Cancer Research, London, United Kingdom.
Minowa et al., "Proteomic analysis of the small intestine and colon epithelia of adenomatous polyposis coli gene-mutant mice by two-dimensional gel electrophoresis", Electrophoresis (2000), pp. 1782-1786, 21, Wilely, Hoboken, NJ.
O'Neill et al., "Isoelectric focusing technology quantifies protein signaling in 25 cells", PNAS (Oct. 31, 2006), pp. 16153-16158, 103 (44), PNAS, Washington, DC.
Ono et al., "Identification by eDNA Microarray of Genes Involved in Ovarian Carcinogenesis", Cancer Research (Sep. 15, 2000), pp. 5007-5011, 60, Cancer Research, London, United Kingdom.
Parker et al., "Independent Measurement of MEK Phosphoforms by Capillary Immunoassay", AACR (2008), Cell Biosciences poster.
Simpson et al., "Proteomic analysis of the human colon carcinoma cell line (LIM 1215): Development of a membrane protein database", Electrophoresis (2000), pp. 1707-1732, 21, Wilely, Hoboken, NJ.
Svaren et al., "EGR1 Target Genes in Prostate Carcinoma Cells Identified by Microarray Analysis", The Journal of Biological Chemistry (Dec. 8, 2000), pp. 38524-38531. 275(49), American Society for Biochemistry and Molecular Biology, Inc., Rockville, MD.
Zwick et al., "Receptor tyrosine kinase signalling as a target for cancer intervention strategies", Endocrine-Related Cancer (2001), pp. 161-173, 8, Endocrine Society, Washington, DC.
Felsher et al., "Reversible tumorigenesis by MYC in hematopoietic lineages", Mol Cell., Aug. 4, 1999 pp. 199-207, (2), Cell Press, Cambridge, MA.
Kistner et al., "Doxycycline-mediated quantitative and tissue-specific control of gene expression in transgenic mice", Proc Natl Acad Sci U S A., Oct. 1, 1996, pp. 10933-10938, 93(20), PNAS, Washington, DC.

(56) References Cited

OTHER PUBLICATIONS

Office action dated Jan. 15, 2013 for U.S. Appl. No. 12/757,745.
Office action dated Apr. 22, 2015 for U.S. Appl. No. 12/757,745.
Office action dated Jul. 10, 2014 for U.S. Appl. No. 12/757,745.
Office action dated Jul. 31, 2012 for U.S. Appl. No. 12/757,745.
Roskoski, "Structure and regulation of Kit protein-tyrosine kinase—the stem cell factor receptor", Biochem Biophys Res Commun., Dec. 23, 2005, pp. 1307-1315, 338(3), Elsevier, Amsterdam, Netherlands.
Seifert et al. "PDGF-AB requires PDGF receptor alpha-subunits for high-affinity, but not for low-affinity, binding and signal transduction", Biol Chem., Feb. 25, 1993 pp. 4473-4480, 268(6), American Society for Biochemistry and Molecular Biology, Inc., Rockville, MD.
Towbin et al., "Electrophoretic transfer of proteins from polyacrylamide gels to nitrocellulose sheets: procedure and some applications", Proc Natl Acad Sci U S A., Sep. 7, 1979, pp. 4350-4354, 76(9), PNAS, Washington, DC.

FIG. 1A
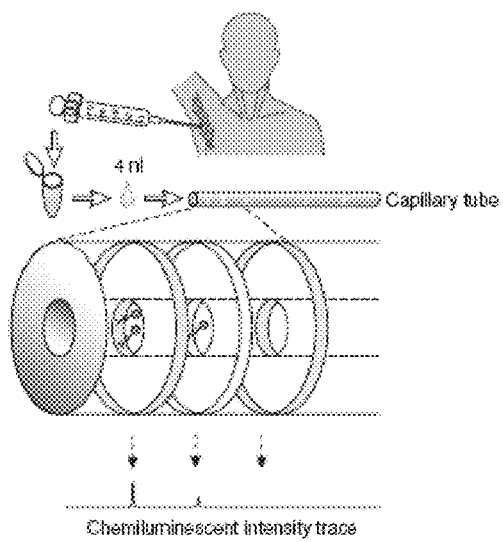
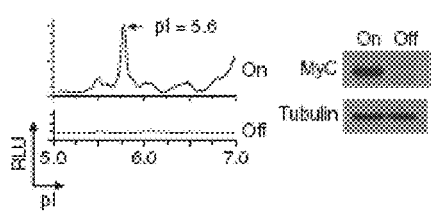
FIG. 1D
FIG. 1B
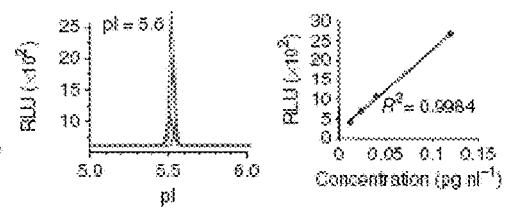
FIG. 1C
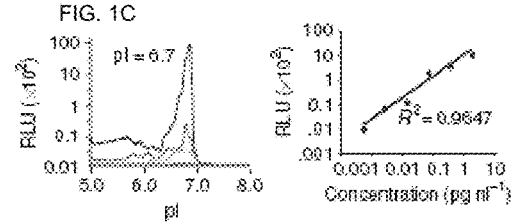
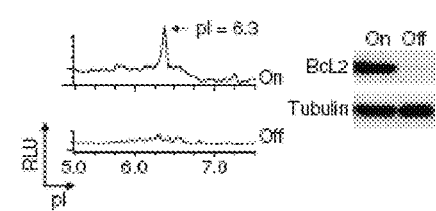
FIG. 1E

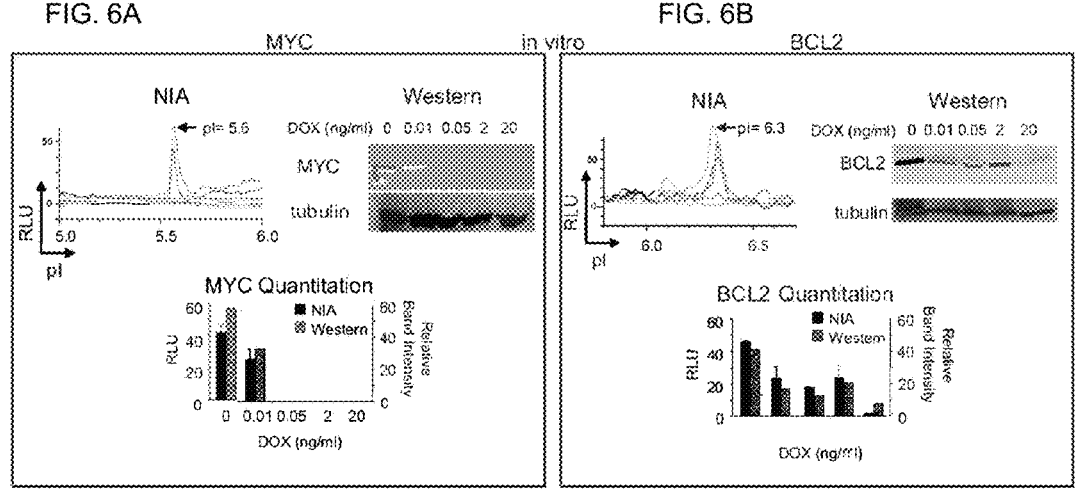

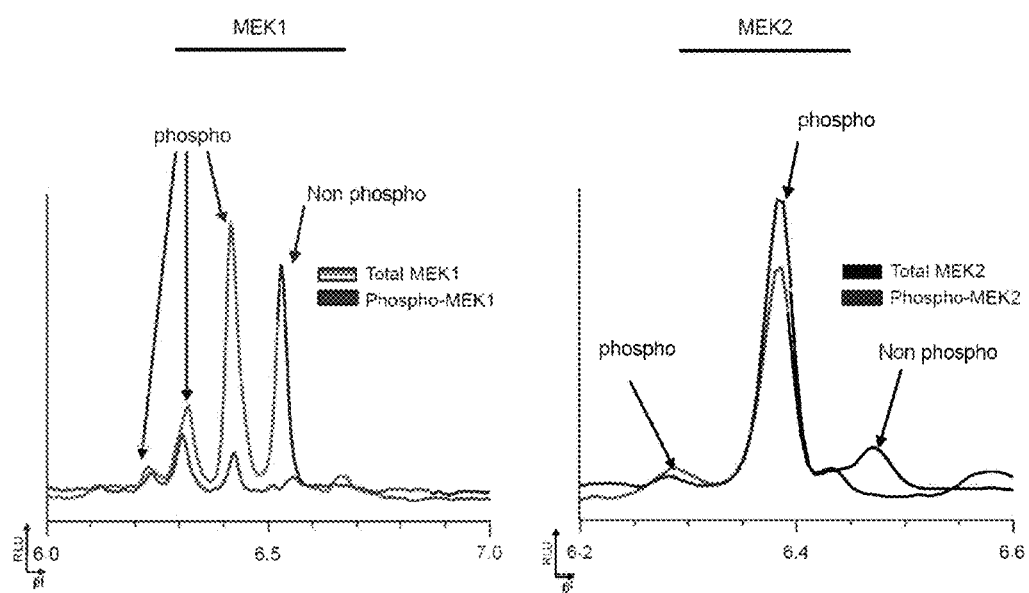

FIG. 12

| Patient | Untreated WBC | Treated WBC | Best Response ||||
| | | | Hematologic* | Cytogenetic* | Molecular* | pERK isoform |
|---|---|---|---|---|---|---|
| 1 | 585.0 | 5.7 | Complete | Minor | N/A | Decrease |
| 2 | 80.4 | 6.1 | Complete | Complete | Major | Decrease |
| 3 | 430.0 | 5.0 | Complete | N/A | N/A | Decrease |
| 4 | 9.3 | 2.3 | Complete | N/A | N/A | Decrease |
| 5 | 21.8 | 5.9 | Complete | Partial | Major | Decrease |
| 6 | 62.4 | 4.7 | Complete | N/A | Complete | Decrease |
| 7 | 106.0 | 5.0 | Partial | N/A | N/A | Decrease |
| 8 | 40.1 | 55.3 | Refractory | Refractory | Refractory | No change |
| 9 | 6.0 | 35.6 | Relapse | Relapse | Relapse | Increase |

\* Response is defined based on guidelines from *Faderl S et al. Ann Intern Med 1999*
N/A= not available

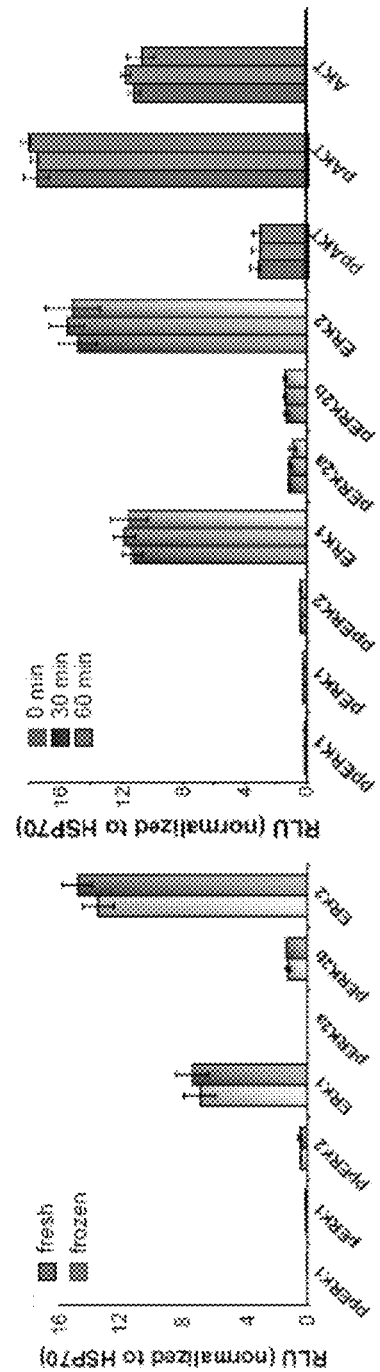

DISCOVERY AND VALIDATION OF CANCER BIOMARKERS USING A PROTEIN ANALYSIS METHODOLOGY TO ANALYZE SPECIMENS

BACKGROUND OF THE INVENTION

The recent explosion of information in the fields of genomics and proteomics has provided a rich ground for the discovery of molecular targets against which therapeutic and/or diagnostic agents can be directed. Tissues for potential target discovery may include tumors and other malignant growths, or infected or inflamed tissues. For example, methods have been described for gene expression profiling of tumor cells (see any one of Ono et al. (2000) *Cancer Res.* 60(18):5007-11; Svaren et al. (2000) *J Biol Chem.*; or Forozan et al. (2000) *Cancer Res.* 60(16):4519-25 for examples). Similarly, proteomics has been used to profile the protein expression in tumor samples (see Minowa et al. (2000) *Electrophoresis* 21(9):1782-6; Cole et al. (2000) *Electrophoresis* 21(9):1772-81; Simpson et al. (2000) *Electrophoresis* 21(9):1707-32); etc.

Cancer is caused by multiple genetic events that result in the activation of proto-oncogenes and/or the inactivation of tumor suppressor genes. In some areas of the world, cancer has become or shortly will become the leading disease-related cause of death of the human population. For example, in the United States, cancer is the second leading cause of death behind cardiovascular disease, and it is projected that cancer will become the leading cause of death within a few years. The medical treatment of cancer still has many unmet needs. Surgery and radiation are generally only successful if the cancer is found at an early, localized stage. Once the disease has progressed to locally advanced cancer or metastatic disease, these therapies are less successful. Existing chemotherapeutic treatments are largely palliative in these advanced tumors, particularly in the case of the common epithelial tumors such as lung, colorectal, breast, prostate, and pancreatic cancers. Although a few chemotherapeutic regimens have yielded lasting remissions or cures (for example, in testicular cancer and childhood leukemias), it is clear that new therapeutic options are necessary.

The transformation and malignant growth of tumor cells is a complex process, which can be variable even within a particular tissue type. Analytical methods that can define the phenotype of tumor cells are useful in determining appropriate therapy, and are therefore of clinical interest. Additionally, knowledge of the mechanism by which a chemotherapeutic agent acts is useful determining optimal formulation and dosage of such agents; in screening for agents effective in treating cancer; and in following patients through a course of treatment.

A variety of post translational modifications of proteins take place. These modifications include phosphorylation, glycosylation, prenylation, and the like. The modifications, particularly reversible phosphorylation, can be a molecular mechanism by which intracellular signals are transmitted. A substantial number of signaling proteins are kinases or phosphatases that act on serine, threonine, and tyrosine residues. Wth over 2000 human genes predicted to code for kinases and the potential for each kinase to act on multiple targets, signaling networks are immensely complex. An important step towards unraveling this complexity is the development of new proteomics technologies that can quantitatively monitor the phosphorylation states of signaling proteins in a multiplex fashion. Such technologies would enable the detailed analysis of signaling pathways in a global perspective and the rapid identification of previously unrecognized signaling events.

Phosphorylation of target proteins by kinases is an important mechanism in signal transduction and for regulating enzyme activity. Tyrosine kinases (TK) are a class of over 100 distinct enzymes that transfer a phosphate group from ATP to a tyrosine residue in a polypeptide (Table 1). Tyrosine kinases phosphorylate signaling, adaptor, enzyme and other polypeptides, causing such polypeptides to transmit signals to activate (or inactive) specific cellular functions and responses. There are two major subtypes of tyrosine kinases, receptor tyrosine kinases and cytoplasmic/non-receptor tyrosine kinases.

To date there have been approximately 60 receptor tyrosine kinases (RTKs; also known as tyrosine receptor kinases (TRK)) described in humans. These kinases are high affinity receptors for hormones, growth factors and cytokines (Robinson et al. (2001) Oncogene 19:5548-57). The binding of hormones, growth factors and/or cytokines generally activates these kinases to promote cell growth and division. Exemplary kinases include insulin-like growth factor receptor, epidermal growth factor receptor, platelet-derived growth factor receptor, etc. Most receptor tyrosine kinases are single subunit receptors but some, for example the insulin receptor, are multimeric complexes. Each monomer contains an extracellular N-terminal region, a single transmembrane spanning domain of 25-38 amino acids, and a C-terminal intracellular domain. The extracellular N-terminal region is composed of a very large protein domain which binds to extracellular ligands e.g. a particular growth factor or hormone. The C-terminal intracellular region provides the kinase activity of these receptors. Receptor tyrosine kinases are key regulators of normal cellular processes and play a critical role in the development and progression of many types of cancer (Zwick et al. (2001) Endocr. Relat. Cancer 8:161-173).

Cancer is frequently associated with the abnormal expression and phosphorylation of oncogenes. Specific tumors may be characterized by the discrete activation of specific oncogenes such as MYC, BCL2 (encoding B cell lymphoma protein-2) and BCR-ABL. Targeted inactivation of oncoproteins is emerging as a specific and effective therapy for cancer. The best known example of a targeted therapy is imatinib mesylate, a small molecule that inactivates several tyrosine kinases, including the BCR-ABL tyrosine kinase in CML. Imatinib treatment results in tumor cell signaling changes in vitro, leading to cell death. In general, the ability to detect specific oncoproteins and their activation state is likely to be highly useful toward the development of new therapeutics as well as in monitoring the effectiveness of these treatments and in evaluating apparent therapeutic resistance[13,21].

Current methods of protein detection are insensitive to detecting subtle changes in oncoprotein activation that underlie key cancer signaling processes. The requirement for large numbers of cells precludes serial tumor sampling for assessing a response to therapeutics. The present invention addresses this need.

SUMMARY OF THE INVENTION

Methods are provided for the analysis, including the serial analysis, of very small amounts of clinical specimens. Samples of interest include human tissue, particularly cancer and other lesions, e.g. blood or solid tumor microbiopsy samples such as fine needle aspirate. Samples may be taken at a single timepoint, or may be taken at multiple timepoints. Samples may be as small as 100,000 cells, as small as 5000 cells, as small as 1000 cells, as small as 100 cells or less.

The methods utilize a nanofluidic proteomic immunoassay (NIA) to quantify total and low-abundance protein isoforms in a small amount of lysate. NIA detection accurately measure oncoprotein expression and activation in limited clinical specimens, including isoforms that differ in post-translational modifications, such as phosphorylation, and the like. The NIA detection method combines isoelectric protein focusing and antibody detection in a nanofluidic system. In some embodiments of the invention, the NIA detection is performed on a sample that has been frozen, where the cells are lysed after thawing. Blood cells may be retained in the sample to reduce variability. Analysis may be performed for up to 60 minutes following sample obtainment, provided the samples are maintained on ice.

In some embodiments of the invention, protein isoform biomarkers are utilized to determine a characteristic of a tumor, including responsiveness to drug treatment. In some embodiments, detection of the presence of the single phosphorylated ERK2 isoform is indicative of responsiveness to tyrosine kinase inhibitors by the cancer, e.g. by chronic myelogenous leukemia cells (CML). The isoform may be detected by NIA, or by conventional methods. In some embodiments of the invention, samples are analyzed by NIA for a 23 member panel of parameters comprising normalized values for: total ERK1/2, phospho-ERK1/2, unphosphorylated ERK1/2, total ERK1, phospho=ERK1, pERK1, ppERK1, unphosphorylated ERK1, total ERK2, phospho-ERK2, pERK1=2, ppERK2, unphosphorylated ERK2; and ERK relative ratios for: % phospho-ERK1/2, % unphosphorylated ERK1/2, % phospho-ERK1, % unphosphorylated ERK1, % phospho-ERK2, % unphosphorylated ERK2, % pERK1, % ppERK1, % pERK2, and % ppERK2.

In some embodiments of the invention, the NIA methods are used to measure changes in cancer cell protein isoforms over time, in response to treatment, etc. Because the methods of the invention only need minimal amounts of specimen, the invention has reduced to practice a minimally invasive protocol for obtaining serial protein profiles after initiating treatment, allowing the determination of predictive protein biomarkers by quantifying early changes in protein activity in patients starting treatment. Analysis of protein change over time in a patient lesion is a better biomarker than any single protein measurement.

In some embodiments, precise measurements of MYC and BCL2 proteins by NIA provide a means of distinguishing lymphoma from normal tissue.

The methods of the invention are of interest for determining patterns of modifications, and the like that define disease states or classify subsets of disease (including staging and subsets of cancers, autoimmune diseases, and the like); that follow response to therapy; that determine response patterns after exposure to a specific agent, and the like. This information is useful in the development of therapies, as a disease prognostic, determining patient specific therapies, and the like.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1E. NIA for the quantitative analysis of oncoproteins. (FIG. 1A) Schematic of the use of NIA for the measurement of oncoproteins from clinical specimens. NIA can be used to measure oncoprotein expression and phosphorylation in clinical specimens, incorporating charge based separation coupled to antibody detection. (FIG. 1B, FIG. 1C) Detection of recombinant MYC (FIG. 1B) or BCL2 (FIG. 1C) oncoproteins in vitro by NIA. Left, representative NIA traces of MYC (black, 0.004 pg nl$^{-1}$; red, 0.012 pg nl$^{-1}$; blue, 0.04 pg nl$^{-1}$; green, 0.12 pg nl$^{-1}$) or BCL2 (green, 0.0019 pg nl$^{-1}$; red, 0.0075 pg nl$^{-1}$; blue, 0.03 pg nl$_{-1}$; orange, 0.12 pg nl$^{-1}$; purple, 0.47 pg nl$^{-1}$; black, 1.8 pg nl$^{-1}$). Right, the data are represented as the normalized peak area versus protein concentration. The calculated correlation coefficients are shown. (FIG. 1D, FIG. 1E) Detection of Myc (FIG. 1D) or Bcl2 (FIG. 1E) oncoproteins in transgenic mouse tumors obtained from serial FNAs by NIA. Serial FNAs were obtained from subcutaneous tumors in mice before (on) and after (off) the suppression of expression of Myc or Bcl2. Right, corresponding western blot analysis. Data are represented as peak areas detected by NIA; mean of three replicates per sample±s.e.m.

(FIG. 2A) Left, representative traces of NIA performed on six clinical biopsy specimens for MYC, BCL2 and HSP-70. Middle, bar graphs showing peak areas detected by NIA; mean of four replicates per sample±s.e.m. Right, western blot analysis of the specimens. (FIG. 2B) Normalized NIA data from a prospective analysis of MYC (top) and BCL2 (bottom) oncoprotein expression in two sets of clinical specimens. Set 1 included eight Burkitt's lymphoma, nine follicular lymphoma, and ten normal samples (the first four normal specimens were benign lymph nodes and the last six normal specimens were control peripheral mononuclear cell samples). Set 2 included seven Burkitt's lymphoma, eleven follicular lymphoma, five marginal zone (MZ) lymphoma and nine DLBCL specimens. Data are represented as the normalized peak areas detected by NIA; mean of four replicates per sample±s.e.m.

(FIG. 4A) Representative NIA traces of total ERK for a subject who responded to treatment. Traces before initiating treatment (left) and during treatment (middle) are shown. The blue box highlights a specific change in the abundance of pERK2 (peak 3). Right, similar results obtained by FACS analysis of clinical specimens. The black box highlights pERK changes detected by FACS. PE, phycoerythrin. (FIG. 4B) Representative NIA traces of total ERK for a subject who failed to respond to treatment, analyzed as in a. (FIG. 4C) Quantification of NIA pERK2 peak 3 analysis of eight subjects before and after initiating treatment. Results are represented as the percentage of pERK2 peak 3 divided by the sum of total phosphorylated and unphosphorylated ERK peaks. Experiments were performed in triplicate.

(FIG. 5A) Schematic for the use of NIA to assess proteomic changes in clinical tumor specimens. Patients undergo pretreatment tumor sampling at baseline and again after 8 d of treatment with atorvastatin. (FIG. 5B) NIA analysis of tumor cells for changes in pSTAT3 and pSTAT5. (FIG. 5C) NIA quantification of pSTAT3 and pSTAT5±s.e.m. Samples were run in triplicate.

FIG. 6A-6B. Sensitivity of NIA versus Western Blot for MYC and BCL2 in Cellular Lysates. (FIG. 6A) The measurement of oncoprotein expression in transgenic mouse tumors. The Tet-off system was used to generate conditional transgenic mouse models of MYC or BCL2 induced lymphomagenesis. Using tumor derived cell lines from these transgenic models, we were able to conditionally regulate the levels of either MYC or BCL2 oncoprotein expression by titrating the concentration of doxycycline (dox) in their growth media. Representative NIA tracings are shown (green=dox 0 ng/ml, blue=0.01 ng/ml, red=0.05 ng/ml, black=2 ng/ml, orange=20 ng/ml). (FIG. 6B) NIA peak height and western blot densitometer quantification are graphed. Corresponding analysis by Western blots is shown. Results obtained were statistically significant for MYC (Pearson correlation R=0.99) and BCL2 (Pearson correlation R=0.94).

(FIG. 7A, FIG. 7C) Left: Representative NIA traces of total ERK and total MEK1 (phosphorylated isoforms are more cationic, black arrows. "p". Unphosphorylated isoforms are labeled "u" in green). Center: NIA quantification for total ERK and total MEK1. Right: Western blot for total ERK and phosphorylated MEK1 in representative Burkitt's lymphoma, follicular lymphoma, and benign lymph tissues are shown. (FIG. 7B, FIG. 7D) Normalized NIA quantitation. NIA pERK and pMEK1 values were normalized against HSP70 values for each of 27 samples (left). Percent pERK and pMEK1 were calculated and graphed (right). All data is represented as the mean of four replicates per sample+/– standard error.

FIG. 8. NIA Peak Identification of MEK1/2 Isoforms. Antibodies specific for total MEK1 (green traces), total MEK2 (black traces), pMEK1 (blue traces) and pMEK2 (red traces) were used to probe K562 cell line using NIA.

(FIG. 10A) NIA detected a change in phospho-ERK in vitro in the K562 CML cell line after treatment with 24 hours with imatinib (peak 3, blue box). pERK was analyzed by Western blot and FACS (FIG. 10B) Peripheral blood tumor cells were isolated from a CML patient before and after initiating imatinib treatment. NIA demonstrates the eradication of pERK2 peak 3 in vivo in a CML patient treated with imatinib. Representative NIA traces obtained in triplicate are shown. (FIG. 10C) NIA Analysis of Total versus Phospho-ERK in CML Patients Treated with Tyrosine Kinase Inhibitors in vivo. Phospho-ERK was measured by NIA using an antibody that detects total (black trace) versus phospho-specific ERK antibody (blue trace). Phospho-ERK2 peak 3 is highlighted by the box.

FIG. 12. Table of best responses.

FIG. 14A-14B. FIG. 14A Freezing the tumor prior to NIA analysis is equivalent to immediate processing and analysis. Representative data of seven ERK isoforms in an FNA lysed immediated after sample collection (fresh) versus a parallel aliquot of the same FNA lysed after storage at −80 degrees C. FIG. 14B Transport time of up to 60 minutes on ice does not affect NIA results. Representative data of ERK and AKT isoforms in FNA kept on ice for 0, 30, or 60 minutes. NIA assays were performed in triplicate.

FIG. 15A Mean percent phosphorylation for each FNA is graphed, +/–SD. FIG. 15B Graph of coefficient of variance (SD/mean) for replicates of each FNA. Each bar is a ratio of: the value of % phospho-ERK for the non-tumor specimen divided by the value of the % phospho-ERK for the paired tumor specimen. The Y-axis of the graph is on a log scale.

FIG. 16A % phospho-Erk is a specific marker for kidney cancer. As shown in the graph, each bar is a ratio of: the value of % phospho-ERK for the non-tumor kidney specimen divided by the value of the % phospho-ERK for the paired kidney tumor specimen. The Y-axis of the graph is on a log scale. FIG. 16B % ppERK1 is a specific marker for head and neck cancer.

DETAILED DESCRIPTION OF THE EMBODIMENTS

Figure 2A:
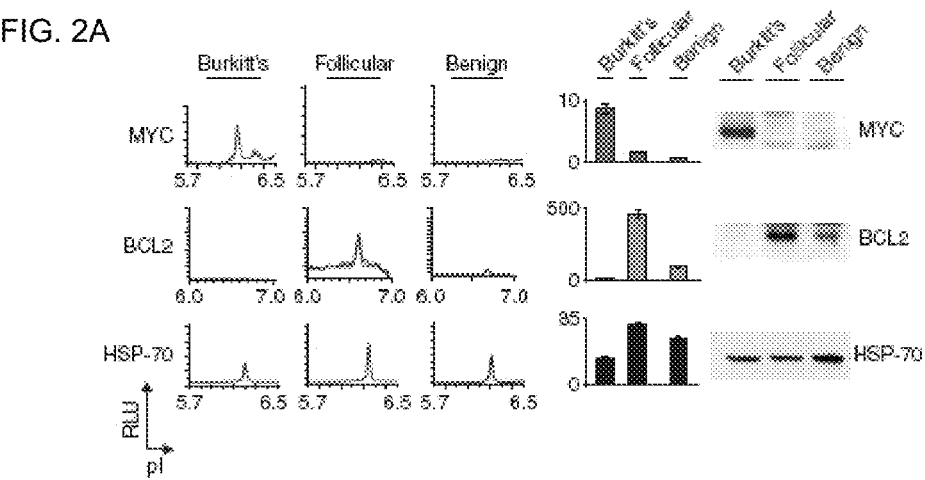
FIG. 2A-2B. NIA for the detection of oncoproteins in human cancer specimens.

Methods are provided for nanofluidic proteomic immunoassay (NIA), including the serial analysis of tissues including cancer and other lesions, e.g. solid tumor microbiopsy samples, lesions involving inflammatory conditions, e.g. MS lesions, synovial fluid of rheumatoid arthritis patients, pancreatic cell samples from IDDM patients, and the like. Samples may be taken at a single timepoint, or may be taken at multiple timepoints. Samples may be as small as 100,000 cells, as small as 5000 cells, as small as 1000 cells, as small as 100 cells or less. NIA detection accurately measure oncoprotein expression and activation in limited clinical specimens, including isoforms that differ in post-translational modifications, such as phosphorylation, and the like. The NIA detection method combines isoelectric protein focusing and antibody detection in a nanofluidic system.

Biopsy samples can be maintained on ice for more than 30 minutes, or more than 60 minutes, usually not more than about 120 minutes following obtention from a patient. The sample is usually maintained without lysis of cells or red blood cells. The sample, or a lysate thereof, is stable when stored frozen at −80 degrees C. for long periods of time. Thus in some embodiments of the invention the analysis is performed on a previously frozen sample.

In some embodiments of the invention, protein isoform biomarkers are utilized to determine a characteristic of a tumor, including responsiveness to drug treatment. Proteins of interest as biomarkers include, without limitation:

| Cell Cycle | Transcription | Apoptosis | Signaling | DNA Repair |
|---|---|---|---|---|
| Cyclin D1, 2, 4 | MYC | p53, MDM2 | RAS | ATM |
| P15, 16, 19 | STAT3/5 | BCL2, BCLxl | MAPK, ERK | ATR |
| RB, 107 | FOS, JUN | Caspases | PI3K, MEK, AKT | H2AX |
| E2F1, 2, 3, 4 | TWIST | TRAIL | JNKs | MRE11 |
| P21 | NFκB | FAD, FAS | CRKL, JAKs | RAD51 |
| | | FoxO | GSK3β | DNAPK |
| | | BIM, BAX | BCR, TCR | ABL |

Protein isoform biomarkers may be utilized to determine a characteristic of a tumor, including responsiveness to drug treatment. In some embodiments, detection of the presence of the single phosphorylated ERK2 isoform is indicative of responsiveness to tyrosine kinase inhibitors by the cancer, e.g. by chronic myelogenous leukemia cells (CML). The isoform may be detected by NIA, or by conventional methods if sample is not limiting.

In some embodiments of the invention, samples are analyzed by NIA for a 23 member panel of parameters comprising normalized values for: total ERK1/2, phospho-ERK1/2, unphosphorylated ERK1/2, total ERK1, phosphor=ERK1, pERK1, ppERK1, unphosphorylated ERK1, total ERK2, phospho-ERK2, pERK1=2, ppERK2, unphosphorylated ERK2; and ERK relative ratios for: % phospho-ERK1/2, % unphosphorylated ERK1/2, % phospho-ERK1, % unphosphorylated ERK1, % phospho-ERK2, % unphosphorylated ERK2, % pERK1, % ppERK1, % pERK2, and % ppERK2. In one embodiment, an initial analysis generates a comprehensive profile of all 23 parameters. The dataset is then analyzed to determine the parameter or parameters that best identifies a tumor of interest, such that in sequent tumor analysis a refined parameter set is chosen.

For relative ratio measurements, a single, pan-specific antibody that recognizes all isoforms of the protein may be used, for example pan-specific ERK antibody, etc. The total amount of the protein, e.g. ERK2, Erk1, etc. is determined, and NIA is used to calculate the percent that is phosphosphorylated. NIA generates peaks, and the area of each peak was calculated by dropping verticals to the baseline at the peak start and end, and summing the area between the start and endpoints. NIA has been shown to be able to discriminate between and quantitate phosphorylated and unphosphorylated isoforms of ERK in a single sample, using a total ERK antibody.

For normalized value measurements a similar process is used, but in addition the assay utilizes an antibody for the protein of interest, e.g. pan-specific ERK antibody, and a loading control antibody, e.g. HSP-70 antibody, and the like, for normalization. NIA is utilized to discriminate the different isoforms.

Figure 16A:
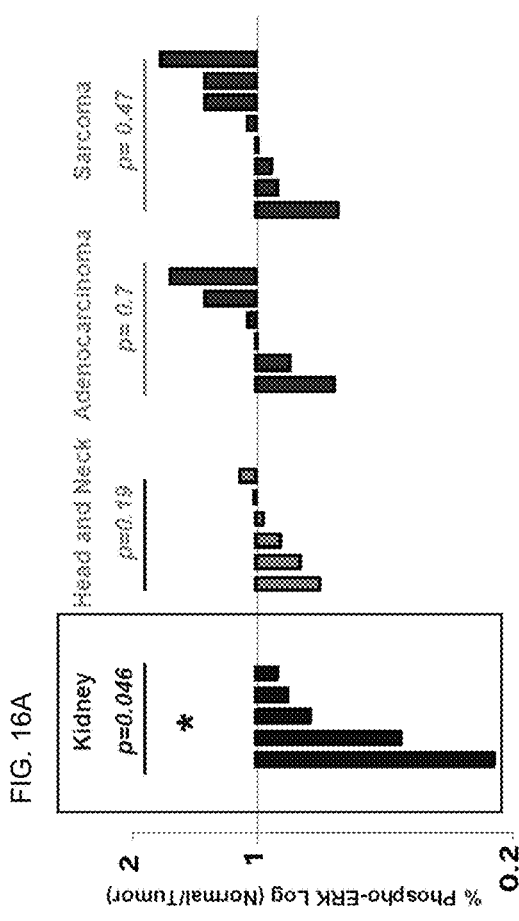
FIG. 16A-16B.
Figure 16B:
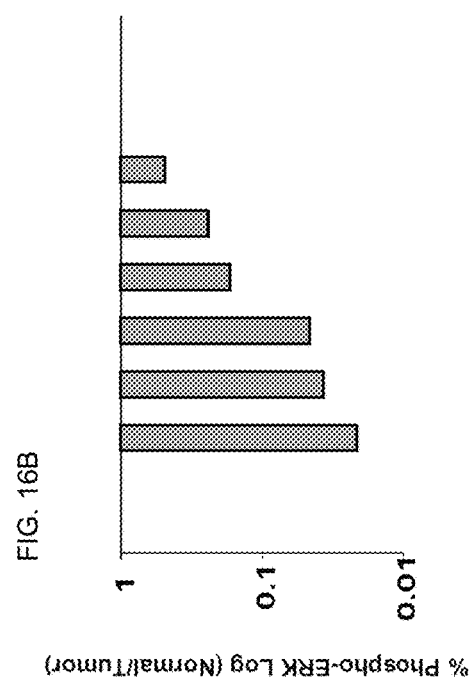

In some embodiments % phospho-ERK is used as a specific biomarker for kidney cancer, for example as shown in FIG. 16A. In other embodiments, % ppERK1 is used as a specific biomarker for head and neck cancer. The control tissue for head and neck cancer will be selected based on the site of the head and neck tumor. For example, salivary gland tumor is paired with the same patient's normal salivary gland. Tongue tumor is paired with the same patient's normal tongue tissue, see FIG. 16B.

Comparisons may be performed between tissue suspected of being a tumor tissue and a paired normal or on-tumor control tissue, e.g. a suspected melanoma or basal cell carcinoma sample, v. an adjacent non-tumor skin sample, and the like. Comparisons may also be performed with reference tumor tissue, with a time series of samples, e.g. before and after treatment, and the like. A ratio may be non-tumor/tumor, or tumor/non-tumor. In some embodiments a ratio provides a more predictive or diagnostic biomarker than a single measurement of tumor or normal.

Mammalian species that provide tissue for analysis include canines; felines; equines; bovines; ovines; etc. and primates, particularly humans. Animal models, particularly small mammals, e.g. murine, lagomorpha, etc. may be used for experimental investigations. Animal models of interest include those for models of tumors, immune responsiveness, and the like.

Regions and/or time points of interest for screening are obtained by needle biopsy or equivalent techniques. The cells are lysed, and the sample proteins are resolved by IEF in a short length of capillary. Resolved proteins are then captured to the capillary wall by photochemically activated molecules lining the capillary. Such immobilization of the proteins allows immune complexes to be formed after the separation step, as a means of specific detection of target proteins. Because the protein-antibody complexes are immobilized in the capillary, chemiluminescence reagents can be flowed through the capillary, and light from the entire capillary can be imaged onto a CCD camera. See, for example, O'Neill et al. (2006) PNAS 103:15153-16158, herein specifically incorporated by reference.

In one embodiment of the invention, the NIA is used to guide selection of patient appropriate agents for therapy. A particular advantage of the invention is the ability to provide individualized diagnosis, taking advantage of small sample size to assess cancer patterns of expression over time.

The information obtained from NIA is used to monitor treatment, modify therapeutic regimens, and to further optimize the selection of therapeutic agents. Wth this approach, therapeutic and/or diagnostic regimens can be individualized and tailored according to the data obtained at different times over the course of treatment.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a compound" includes a plurality of such compounds and reference to "the agent" includes reference to one or more agents and equivalents thereof known to those skilled in the art, and so forth. All technical and scientific terms used herein have the same meaning as commonly understood to one of ordinary skill in the art to which this invention belongs unless clearly indicated otherwise.

Post-Translational Modification

Glycosylation.

Among the post-translational modifications that can be probed, are protein specific glycoslyation. Membrane associated carbohydrate is exclusively in the form of oliogsaccharides covalently attached to proteins forming glycoproteins, and to a lesser extent covalently attached to lipid forming the glycolipids. Glycoproteins consist of proteins covalently linked to carbohydrate. The predominant sugars found in glycoproteins are glucose, galactose, mannose, fucose, GalNAc, GlcNAc and NANA. The distinction between proteoglycans and glycoproteins resides in the level and types of carbohydrate modification. The carbohydrate modifications found in glycoproteins are rarely complex: carbohydrates are linked to the protein component through either O-glycosidic or N-glycosidic bonds. The N-glycosidic linkage is through the amide group of asparagine. The O-glycosidic linkage is to the hydroxyl of serine, threonine or hydroxylysine. The linkage of carbohydrate to hydroxylysine is generally found only in the collagens. The linkage of carbohydrate to 5-hydroxylysine is either the single sugar galactose or the disaccharide glucosylgalactose. In ser- and thr-type O-linked glycoproteins, the carbohydrate directly attached to the protein is GalNAc. In N-linked glycoproteins, it is GlcNAc.

The predominant carbohydrate attachment in glycoproteins of mammalian cells is via N-glycosidic linkage. N-linked glycoproteins all contain a common core of carbohydrate attached to the polypeptide. This core consists of three mannose residues and two GlcNAc. A variety of other sugars are attached to this core and comprise three major N-linked families: High-mannose type contains all mannose outside the core in varying amounts; hybrid type contains various sugars and amino sugars; complex type is similar to the hybrid type, but in addition, contains sialic acids to varying degrees.

Acylation.

Many proteins are modified at their N-termini following synthesis. In most cases the initiator methionine is hydrolyzed and an acetyl group is added to the new N-terminal amino acid. Some proteins have the 14 carbon myristoyl group added to their N-termini. The donor for this modification is myristoyl-CoA. This latter modification allows association of the modified protein with membranes. For example, the catalytic subunit of cyclicAMP-dependent protein kinase (PKA) is myristoylated.

Methylation.

Post-translational methylation occurs at lysine residues in some proteins such as calmodulin and cytochrome c. The activated methyl donor is S-adenosylmethionine.

Phosphorylation.

Post-translational phosphorylation is one of the most common protein modifications that occurs in animal cells. The vast majority of phosphorylations occur as a mechanism to regulate the biological activity of a protein and as such are transient. In animal cells serine, threonine and tyrosine are the amino acids subject to phosphorylation. The largest group of kinases are those that phosphorylate either serines or threonines and as such are termed serine/threonine kinases. The ratio of phosphorylation of the three different amino acids is approximately 1000/100/1 for serine/threonine/tyrosine. Although the level of tyrosine phosphorylation is minor, the importance of phosphorylation of this amino acid is profound. As an example, the activity of numerous growth factor receptors is controlled by tyrosine phosphorylation.

Sulfation.

Sulfate modification of proteins occurs at tyrosine residues such as in fibrinogen and in some secreted proteins, e.g. gastrin. The universal sulfate donor is 3'-phosphoadenosyl-5'-phosphosulphate (PAPS).

Prenylation.

Prenylation refers to the addition of the 15 carbon farnesyl group or the 20 carbon geranylgeranyl group to acceptor proteins, both of which are isoprenoid compounds derived from the cholesterol biosynthetic pathway. The isoprenoid groups are attached to cysteine residues at the carboxy terminus of proteins in a thioether linkage (C-S-C). A common consensus sequence at the C-terminus of prenylated proteins has been identified and is composed of CAAX, where C is cysteine, A is any aliphatic amino acid (except alanine) and X is the C-terminal amino acid. In order for the prenylation reaction to occur the three C-terminal amino acids (AAX) are first removed and the cysteine activated by methylation in a reaction utilizing S-adenosylmethionine as the methyl donor. Important examples of prenylated proteins include the oncogenic GTP-binding and hydrolyzing protein Ras and the g-subunit of the visual protein transducin, both of which are farnesylated. Numerous GTP-binding and hydrolyzing proteins (termed G-proteins) of signal transduction cascades have g-subunits modified by geranylgeranylation.

Vitamin C-Dependent Modifications.

Modifications of proteins that depend upon vitamin C as a cofactor include proline and lysine hydroxylations and carboxy terminal amidation. The hydroxylating enzymes are identified as prolyl hydroxylase and lysyl hydroxylase. The donor of the amide for C-terminal amidation is glycine. The most important hydroxylated proteins are the collagens. Several peptide hormones such as oxytocin and vasopressin have C-terminal amidation.

Vitamin K-Dependent Modifications.

Vitamin K is a cofactor in the carboxylation of glutamic acid residues. The result of this type of reaction is the formation of a γ-carboxyglutamate (gamma-carboxyglutamate), referred to as a gla residue. The formation of gla residues within several proteins of the blood clotting cascade is critical for their normal function. The presence of gla residues allows the protein to chelate calcium ions and thereby render an altered conformation and biological activity to the protein. The coumarin-based anticoagulants, warfarin and dicumarol function by inhibiting the carboxylation reaction.

Selenoproteins.

Selenium is a trace element and is found as a component of several prokaryotic and eukaryotic enzymes that are involved in redox reactions. The selenium in these selenoproteins is incorporated as a unique amino acid, selenocysteine, during translation. A particularly important eukaryotic selenoenzyme is glutathione peroxidase. This enzyme is required during the oxidation of glutathione by hydrogen peroxide ($H_2O_2$) and organic hydroperoxides. Incorporation of selenocysteine by the translational machinery occurs via an interesting and unique mechanism. The tRNA for selenocysteine is charged with serine and then enzymatically selenylated to produce the selenocysteinyl-tRNA. The anticodon of selenocysteinyl-tRNA interacts with a stop codon in the mRNA (UGA) instead of a serine codon. The selenocysteinyl-tRNA has a unique structure that is not recognized by the termination machinery and is brought into the ribosome by a dedicated specific elongation factor. An element in the 3' non-translated region (UTR) of selenoprotein mRNAs determines whether UGA is read as a stop codon or as a selenocysteine codon.

In some embodiments to the invention a cancer, e.g. CML, is classified according to responsiveness to a tyrosine kinase inhibitor, e.g. "class III tyrosine kinase receptors", which refers to a subclass of receptor tyrosine kinases (RTKs). Imatinib is exemplary as an inhibitor. The class III RTKs, which include PDGFRa, PDGFRb, c-Fms, c-Kit and Fms-like tyrosine kinase 3 (Flt-3), are distinguished from other classes of RTKs in having five immunoglobulin-like domains within their extracellular binding site as well as a 70-100 amino acid insert within the kinase domain (Roskoski, R. (2005) *Biochem. Biophys. Res. Commun.* 338:1307-15). Structural similarities among class III RTKs results in cross-reactivity with respect to ligands, as evidenced in the case of imatinib blocking PDGFRa, PDGFRb, c-Fms, and c-Kit.

Platelet-derived growth factor receptors (PDGFR) include PDGFR-alpha (PDGFRa) and the PDGFR-beta (PDGFRβ) (Yu, J. et al, (2001) *Biochem Biophys Res Commun.* 282: 697-700). The PDGF B-chain homodimer PDGF BB activates both PDGFRα and PDGFRβ, and promotes proliferation, migration and other cellular functions in fibroblast, smooth muscle and other cells. The PDGF-A chain homodimer PDGF AA activates PDGFRα only. PDGF-AB binds PDGFRα with high-affinity and in the absence of PDGFRα can bind at a lower affinity (Seifert, R. A., et al, (1993), J Biol Chem. 268(6):4473-80). Recently, additional PDGFR ligands have been identified including PDGF-CC and PDGF-DD. Fibroblasts and other mesenchymal cells express fibroblast-growth factor receptor (FGFR) which mediates tissue repair, wound healing, angiogenesis and other cellular functions.

Cells.

Cells for use in the assays of the invention can be an organism, a tissue sample, including a biopsy sample, etc. The invention is suitable for use with any cell type, including primary cells, biopsy tissue Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc.

Tumors of interest for imaging include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Lysates.

The cells, which may be cells after exposure to an agent or condition of interest, are lysed prior to analysis. Methods of lysis are known in the art, including sonication, non-ionic surfactants, etc. Non-ionic surfactants include the Triton™ family of detergents, e.g. Triton™ X-15; Triton™ X-35; Triton™ X-45; Triton™ X-100; Triton™ X-102; Triton™ X-114; Triton™ X-165, etc. Brij™ detergents are also similar in structure to Triton™ X detergents in that they have varying lengths of polyoxyethylene chains attached to a hydrophobic chain. The Tween™ detergents are nondenaturing, nonionic detergents, which are polyoxyethylene sorbitan esters of fatty acids. Tween™ 80 is derived from oleic acid with a $C_{18}$ chain while Tween™ 20 is derived from lauric acid with a $C_{12}$ chain. The zwitterionic detergent, CHAPS, is a sulfobetaine derivative of cholic acid. This zwitterionic detergent is useful for membrane protein solubilization when protein activity is important. The surfactant is contacted with the cells for a period of time sufficient to lyse the cells and remove additional adherent cells from the system.

Methods of cellular fractionation are also known in the art. Subcellular fractionation consists of two major steps, disruption of the cellular organization (lysis) and fractionation of the homogenate to separate the different populations of organelles. Such a homogenate can then be resolved by differential centrifugation into several fractions containing mainly (1) nuclei, heavy mitochondria, cytoskeletal networks, and plasma membrane; (2) light mitochondria, lysosomes, and peroxisomes; (3) Golgi apparatus, endosomes and microsomes, and endoplasmic reticulum (ER); and (4) cytosol. Each population of organelles is characterized by size, density, charge, and other properties on which the separation relies.

The isoelectricly focused protein is bound to a specific binding member. The term "specific binding member" as used herein refers to a member of a specific binding pair, i.e. two molecules, usually two different molecules, where one of the molecules through chemical or physical means specifically binds to the other molecule. The complementary members of a specific binding pair are sometimes referred to as a ligand and receptor; or receptor and counter-receptor.

Binding pairs of interest include antigen and antibody specific binding pairs, peptide-MHC-antigen complexes and T cell receptor pairs, biotin and avidin or streptavidin; carbohydrates and lectins; complementary nucleotide sequences; peptide ligands and receptor; effector and receptor molecules; hormones and hormone binding protein; enzyme cofactors and enzymes; enzyme inhibitors and enzymes; and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies; and T cell antigen receptors, and their cognate MHC-peptide conjugates. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

The binding member may be directly or indirectly labeled with an optically detectable label, usually a chemiluminescent label. Of interest as a label are fluorophores. Fluorescence is a physical phenomenon based upon the ability of some molecules to absorb and emit light. With some molecules, the absorption of light at specified wavelengths is followed by the emission of light from the molecule of a longer wavelength and at a lower energy state. Such emissions are called fluorescence and the emission lifetime is said to be the average period of time the molecule remains in an excited energy state before it emits light of the longer wavelength. Substances that release significant amounts of fluorescent light are termed "fluorophores". This broad class includes fluorescein isothiocyanate (FITC), fluorescein di-galactose (FDG); lissamine, rhodamine, Texas Red, phycoerythrin, allophycocyanin, 6-carboxyfluorescein (6-FAM), 2,7-dimethoxy-4,5-dichloro-6-carboxyfluorescein (6-JOE), 6-carboxy-X-rhodamine (6-ROX), 6-carboxy-2,4,4',5',7,7'-hexachlorofluorescein (6-HEX), 5-carboxyfluorescein (5-FAM) or N,N,N,N-tetramethyl-6-carboxyrhodamine (6-TAMRA); dansyl chloride; naphthylamine sulfonic acids such as 1-anilino-8-naphthalene sulfonic acid ("ANS") and 2-p-toluidinylnaphthalene-6-sulfonic acid ("TNS") and their derivatives; acridine orange; proflavin; ethidium bromide; quinacrine chloride; and the like.

The specific binding partner will bind with a cellular parameter of interest. Parameters may include a variety of post-translational modifications, e.g. phosphoserine, phosphotyrosine; acyl groups, etc. In addition to, or in combination with, a parameter can be any cell component or cell product including receptor, protein or conformational or posttranslational modification thereof, lipid, carbohydrate, organic or inorganic molecule, nucleic acid, e.g. mRNA, DNA, etc. or a portion derived from such a cell component or combinations thereof. Parameters may provide a quantitative readout, in some instances a semi-quantitative or qualitative result.

Parameters of interest include detection of cytoplasmic biomolecules, frequently biopolymers, e.g. polypeptides, polysaccharides, polynucleotides, lipids, etc. In one embodiment, parameters include specific epitopes. Epitopes are frequently identified using specific monoclonal antibodies or receptor probes. A parameter may be defined by a specific monoclonal antibody or a ligand or receptor binding determinant.

Of interest for the methods of the invention are cells before, after and/or during exposure to an agent or agents of interest. Candidate biologically active agents may encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetic agents, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Methods

A patient lesion is analyzed through any the methods described above. The tissue samples are analyzed for the presence of variations in proteomic biomarkers, e.g. changes in the total amount, or as a percent of total proteins of a particular isoform, which isoform may be differentially phosphorylated, glycosylated, prenylated, etc. As described above, the analysis will utilize a high throughput system for analysis. The sample may be compared to samples from other regions of the lesion, to earlier time points in the disease, to normal tissues of similar type, and the like.

The information about an individual patient from the analysis is useful in therapeutic uses, where therapy can be adjusted to utilize the optimal molecular targets, and can then be monitored over time.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

In order to accurately measure oncoprotein expression and activation in limited clinical specimens, we have developed a nano-fluidic proteomic immunoassay detection method (NIA) that combines isoelectric protein focusing and antibody detection. Here we demonstrate that we can use this new technique to quantitate oncoprotein expression and phosphorylation in clinical specimens to precisely measure specific changes in phospho-isomers of oncoproteins in vitro and in vivo.

Results

NIA Detection of Oncoprotein Expression in Clinical Specimens. NIA incorporates isoelectric focusing of proteins, followed by antibody detection of specific epitopes with chemiluminescence. The chemiluminescent signal is rendered as a chemiluminescence isoelectropherogram (trace) of "relative luminescence units (RLU)" on the y-axis vs. isoelectric point (pI) on the x-axis (FIG. 1a). As little as 2 picograms of MYC could be detected using 4 nanoliters of recombinant protein per capillary (final capillary concentration 0.004-0.12 pg/nl) at the expected isoelectric point (pI) of 5.6 with a linear response (FIG. 1b, $R^2=0.9984$). Concentrations of BCL2 could be detected over up to a 3-log dynamic range at pI 6.7 (FIG. 1c, $R^2=0.9647$). Therefore, NIA is highly quantitative and sensitive over a large dynamic range.

Next, we assessed the ability to detect oncoproteins in tumor cell lines both in vitro and in vivo. Previously, we have described the generation of a conditional transgenic lymphoma model that uses the Tet-off system to regulate oncoprotein expression. In our tumor derived cell lines, MYC and BCL2 were readily detected by NIA, comparable to Western analysis (FIG. 6). Each oncoprotein measurement from these tumor lysates exhibited a characteristic peak profile defined by how post-translational modifications influence its isoelectric point. The profile obtained from mouse tumor lines was different from the recombinant BCL2 described above because NIA is exquisitely sensitive to the cationic charge associated with the histidine tag of the recombinant protein. Our results elaborate how NIA can distinguish and measure oncoprotein expression from tumor cell lines.

To evaluate if we could quantitatively detect oncoprotein expression in vivo, conditional mouse tumor-derived cell lines were inoculated into syngeneic mice. Examination of serial tumor samples by fine needle aspiration (FNA) confirmed that both MYC and BCL2 expression could be readily detected and quantitated in vivo by NIA with results comparable to Western analysis (FIG. 1d, e). To measure oncoprotein expression in human tumors, MYC and BCL2 levels were measured in four lymphomas and two benign lymph nodes. High levels of MYC protein commonly associated with Burkitt's lymphoma and high levels of BCL2 characteristic of follicular lymphoma were detected (FIG. 2a). Thus, NIA can reproducibly detect changes in oncoprotein expression even from limited clinical biopsy specimens in mouse or human tumor specimens both in vitro and in vivo.

Our results suggested that we may be able to precisely quantify levels of oncoproteins in clinical specimens. Analysis was performed on a set of 27 human specimens that included Burkitt's lymphoma, follicular lymphoma, benign lymph nodes, or normal peripheral blood mononuclear cells (PBMC's) (set 1, FIG. 2b, c). In our first series (set 1), Burkitt's lymphoma samples expressed MYC at a level higher than all of the other sample groups (Mann Whitney test, p<0.0001). All Burkitt's lymphoma specimens had a MYC level greater than 0.2 RLU, compared with 11% of follicular lymphoma. Follicular lymphoma samples expressed significantly higher BCL2 than all other sample groups (Mann Whitney test, p<0.0001); 89% of follicular lymphoma patients had a BCL2 level higher than 0.06 RLU, compared with none of the Burkitt's patients. BCL2 was detectable and quantifiable even in normal specimens. NIA was quantitative enough to distinguish statistically significant differences in oncoprotein expression between lymphomas.

Figure 2B:
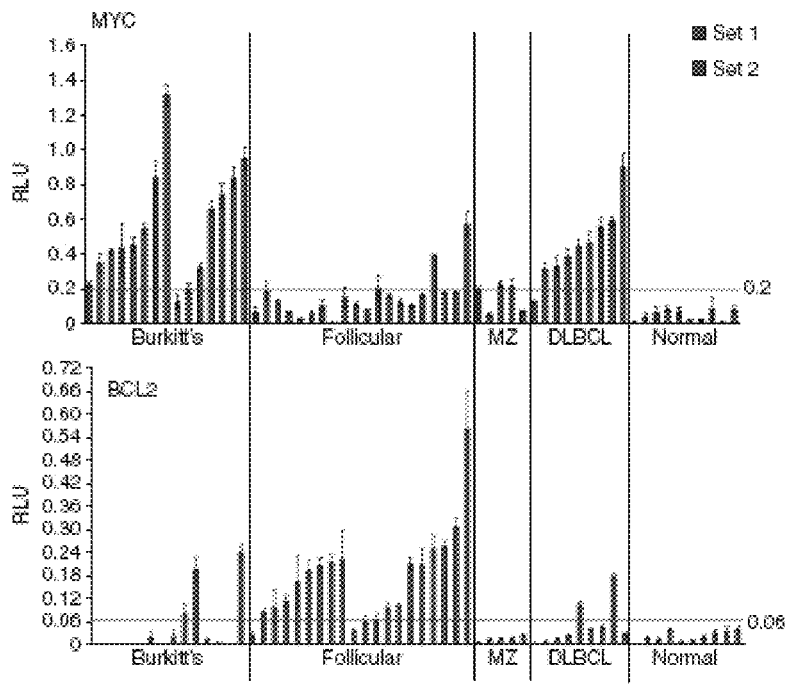

To validate our results, we next quantified MYC and BCL2 in a new series of clinical specimens including seven Burkitt's lymphoma, 11 follicular lymphoma, nine diffuse large B cell lymphoma (DLBCL) and five marginal zone lymphoma (MZ) specimens (FIG. 2b, c, set 2). We confirmed that the MYC threshold of 0.2 RLU and the BCL2 threshold of 0.06 RLU were statistically significant for distinguishing Burkitt's from follicular lymphoma (Fisher's exact test, two tailed: p=0.0498 and 0.0474, respectively). We observed that two of nine DLBCL tumors overexpressed BCL2 and many tumors expressed high increased levels of MYC. In contrast, marginal zone lymphomas expressed a low mean level of 0.18 RLU MYC. Hence, we found different levels of MYC and BCL2 expression in 44 of 49 tumor specimens when compared with normal controls.

Figure 7A:
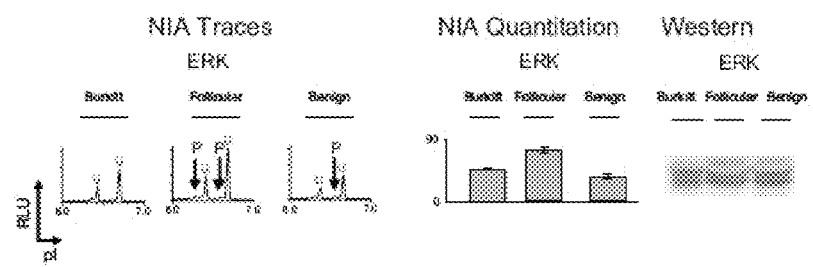
FIG. 7A-7D. NIA Analysis of ERK and MEK1 Isoforms in a Panel of 27 Lymphoma and Control Specimens. NIA was used to measure phosphorylated and unphosphorylated isoforms of ERK and MEK1 in clinical patient specimens.
Figure 7B:
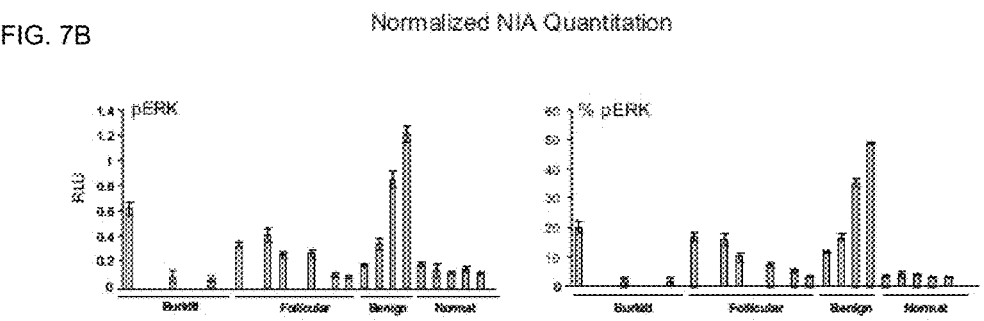
Figure 7C:
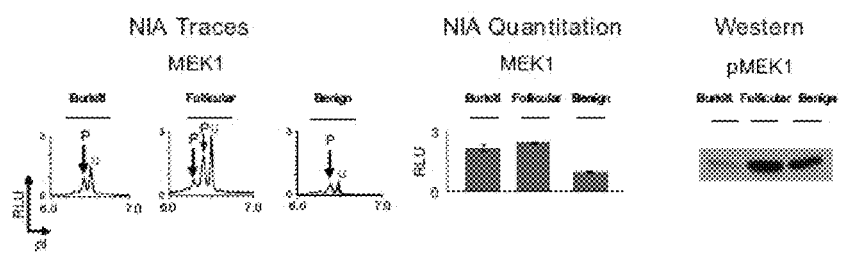
Figure 7D:
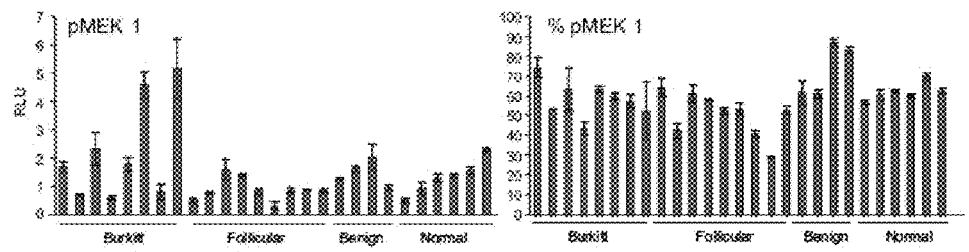

NIA Measurement of Oncoprotein Phosphorylation in Clinical Specimens. An important feature of NIA is that it can be used to identify phosphorylated isoforms of a protein. ERK and distinct patterns of phospho-isomers were detected in the normal and lymphoma specimens (FIG. 7a). Next, we identified MEK 1 and MEK 2 isomers (FIGS. 7b and 8). Experiments were performed in quadruplicate and were highly reproducible. We could detect as little as a 10% difference in phosphorylated ERK and MEK. Our results show that NIA is highly sensitive, reproducible and quantitative.

Figure 3:
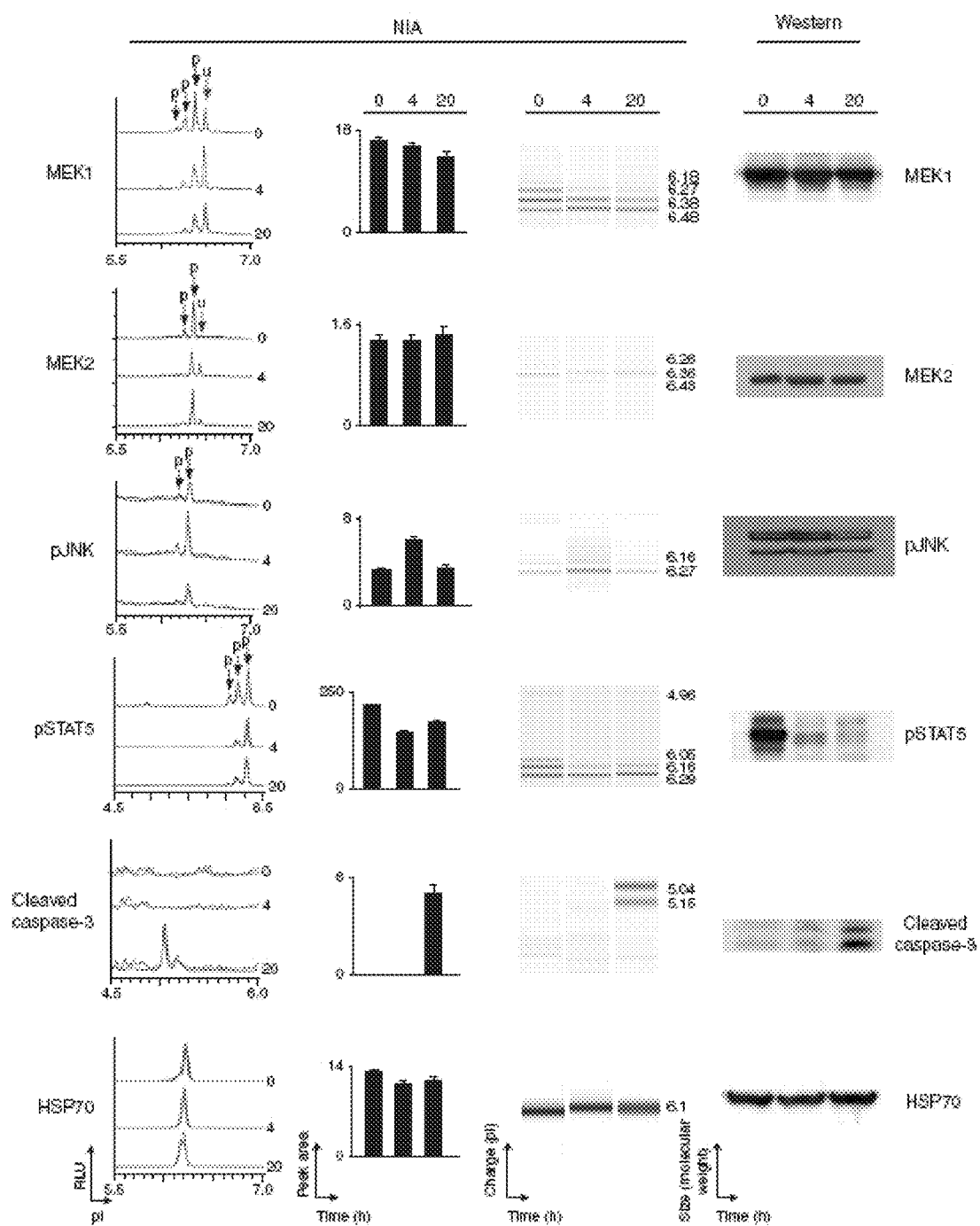
FIG. 3. NIA detection of changes in oncoprotein activation in CML cells treated with imatinib. NIA was used to quantify proteomic changes in the K562 cell line treated with imatinib in vitro for 0 h, 4 h and 20 h. MEK1, MEK2, phospho-JNK (pJNK), pSTAT5 and activated caspase-3 were detected by NIA. From left to right: representative traces for the protein of interest, bar graph of NIA quantification of each protein, NIA pseudoblot representation and western blot data. Peaks on the traces that represent phosphorylated isoforms are indicated with black arrows. All measurements were performed in six replicates, and bar graph data are represented as the mean peak area±s.e.m.
Figure 9:
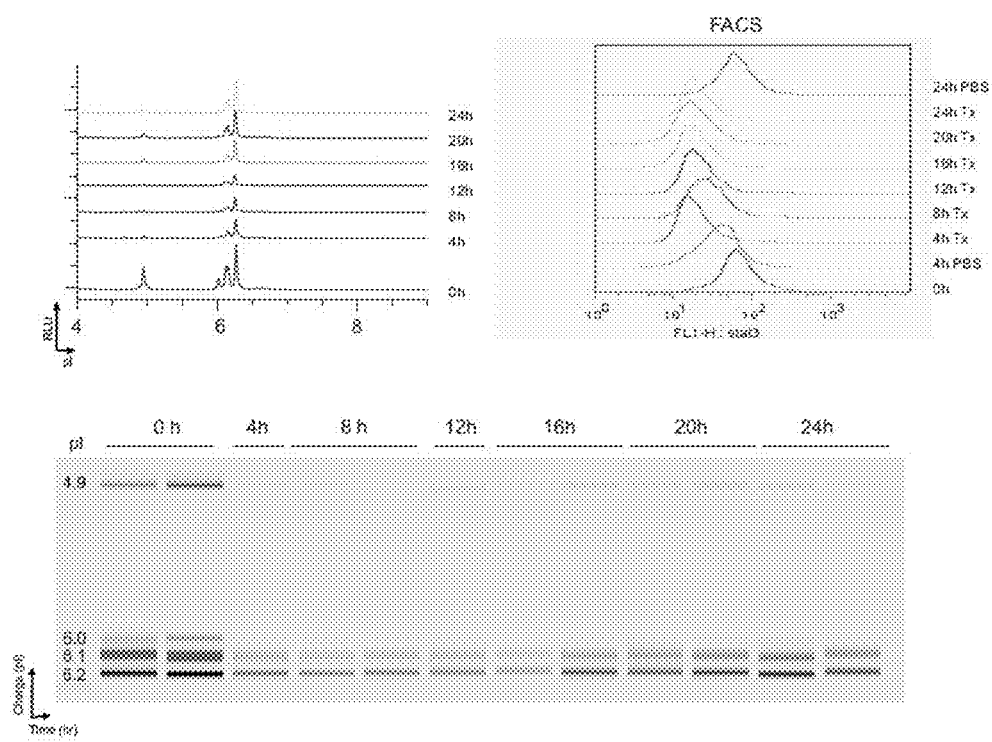
FIG. 9. NIA Analysis of STAT3 Phosphorylation Following Imatinib Treatment in vitro. pSTAT3 was measured by NIA or FACS in K562 cells treated with imatinib or PBS for 0, 4, 8, 12, 16, 20 or 24 h in vitro.
Figure 10A:
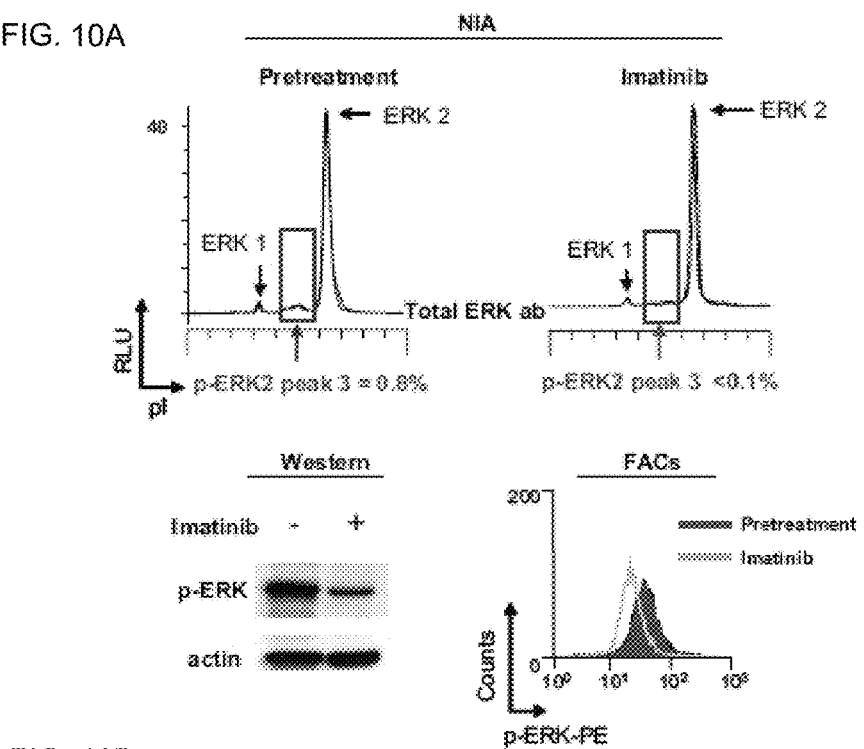
FIG. 10A-10C. NIA Identifies a Decrease in a Specific Phospho-ERK Isoform upon Imatinib Treatment in vitro and in vivo.

Next, we evaluated if we could detect specific protein signaling changes in human tumors in response to targeted therapy. Treatment of the K562 human CML cell line with imatinib in vitro resulted in changes in phosphorylation of STAT3/5, JNK, MEK1 and MEK2 and an expected increase in activated caspase-3 associated with apoptosis (FIG. 3, FIG. 9). To facilitate comparison with Western blot results, data was converted into a "pseudo-blot" representation. In a pseudo-blot, the area under each NIA peak is represented as a band at the corresponding isoelectric point. By visualizing different isoforms we were able to identify that imatinib treatment was associated with a decrease in a specific ERK2 phospho-isomer (FIG. 10a). Thus, NIA appeared to detect a unique signaling change in response to the targeted therapeutic agent, imatinib.

Figure 4A:
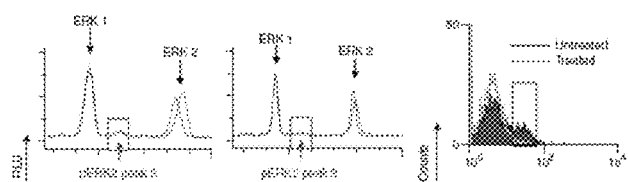
FIG. 4A-4C. NIA detected changes in pERK in individuals with CML who responded to imatinib treatment.
Figure 4B:
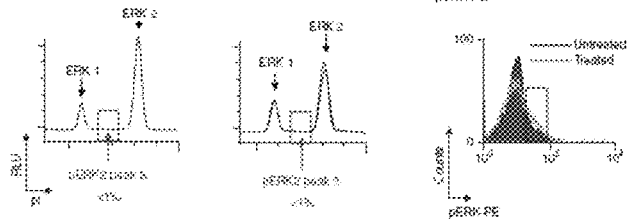
Figure 4C:
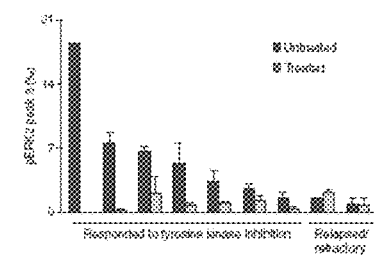
Figure 5A:
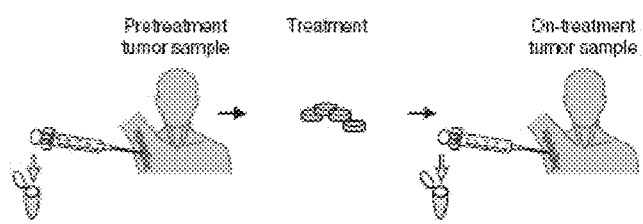
FIG. 5A-5C. NIA detected decrease in oncoproteins upon treatment with biologic response modifying therapeutic agent.
Figure 5B:
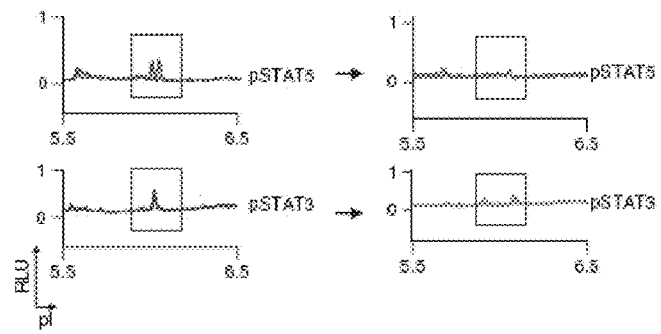
Figure 5C:
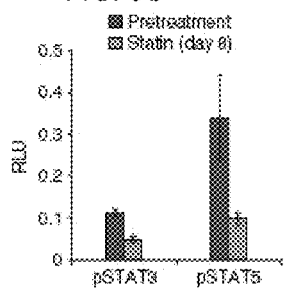
Figure 10B:
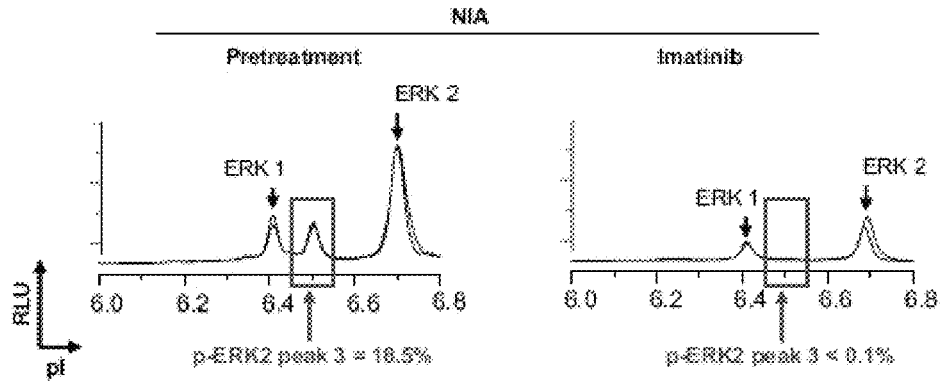
Figure 10C:
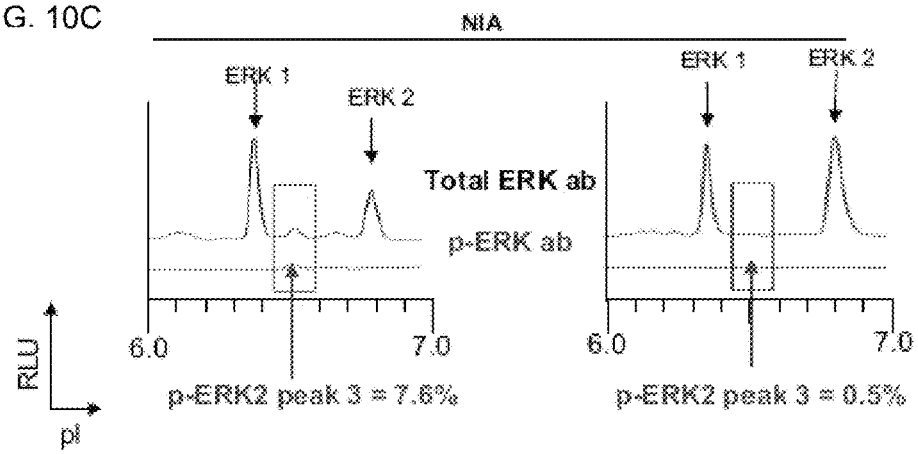
Figure 11:
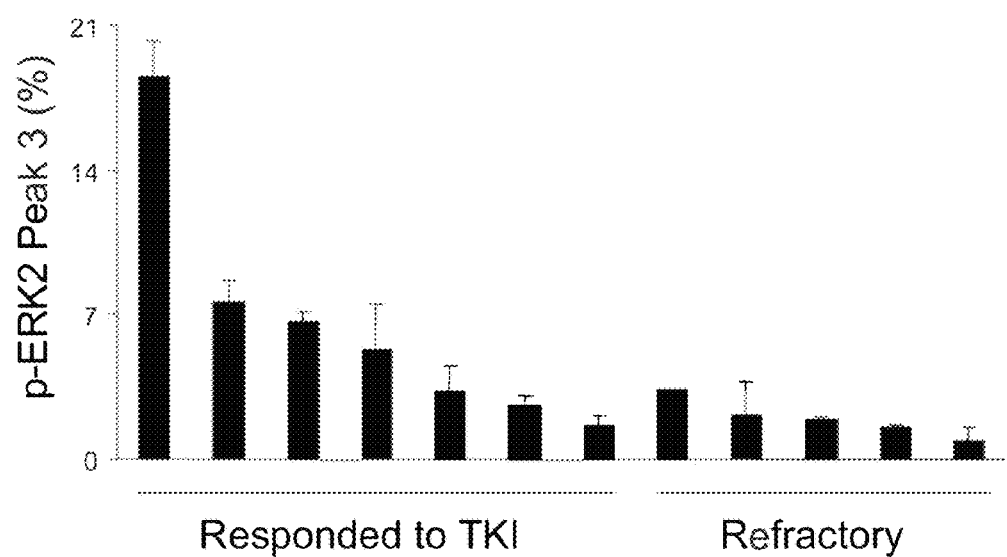
FIG. 11. Comparison of Basal pERK2 in Patients with CML. Basal p-ERK2 values are graphed for 7 patients that subsequently responded to TKI ("responded to TKI"), and 5 patients that subsequently did not respond to TKI treatment ("refractory"). There is no statistically significant difference between the mean values for each group (unpaired t-test, 2 tailed, p=0.1678). Mean value for each patient+/–SEM of experiments performed in triplicate are graphed.
Figure 13A:
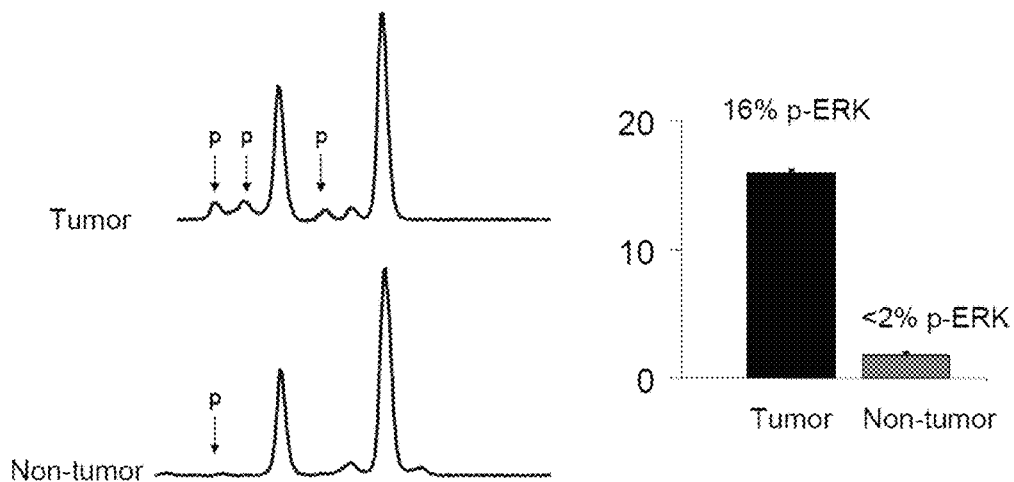
FIG. 13A-13B. NIA of total ERK in resected carcinoma.
Figure 13B:
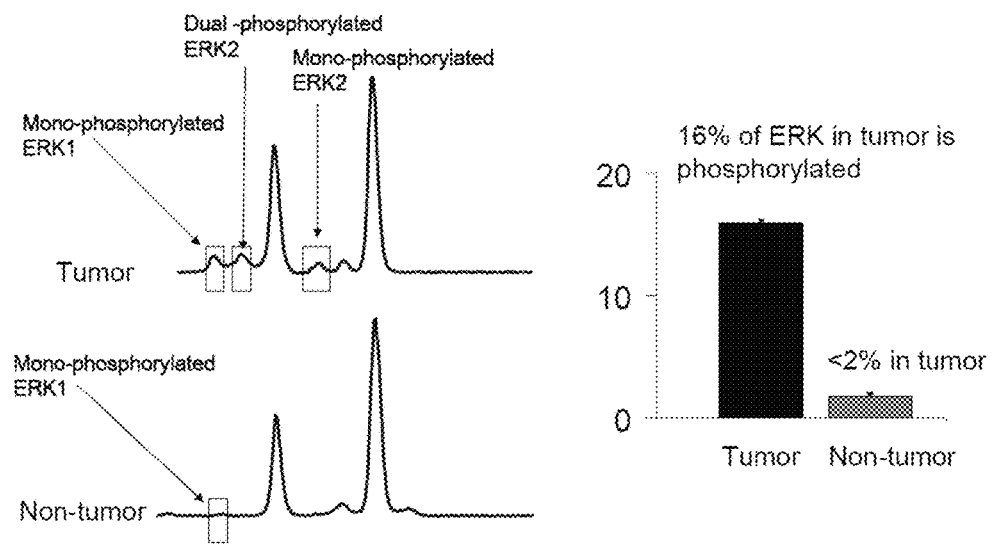

To evaluate if we could identify changes in protein signaling in vivo in clinical specimens, we measured changes in oncoprotein signaling in the tumor cells in the peripheral blood of CML patients treated with tyrosine kinase inhibitors. All seven patients that responded to tyrosine kinase inhibitor therapy exhibited a 54-100% decrease in a mono-phosphorylated ERK2 isoform (note peak 3; FIG. 4a and FIGS. 10b, c), whereas two patients that were resistant to tyrosine kinase inhibitor therapy did not (FIG. 4c, table 1). Although basal ERK2 expression was not different (FIG. 11), the relative fold-change in ERK2 phosphorylation was different between CML patients that respond versus those that did not (unpaired t-test, 2 tailed=0.0007). Thus, NIA has identified a specific change in ERK phosphorylation that is associated with a clinical response to effective therapy.

Finally, we interrogated if NIA could be used to serially monitor the response of a patient's tumor to a potential biologic response modifier in vivo. Recently, we described that atorvastatin treatment causes tumor regression associated with specific changes in oncoprotein signaling in a mouse model of lymphoma. We investigated if atorvastatin has biological activity in human patients with lymphoma.

We could demonstrate that patients treated with atorvastatin exhibited detectable decreases in phosphorylation of STAT3/5 after eight days of treatment (FIG. 7). Thus, we found that atorvastatin has unanticipated in vivo biologic activity against human lymphoma cells.

We have developed the application of a highly sensitive and reproducible nanoscale technology to measure oncoprotein expression and phosphorylation and to identify the biological response to therapeutics. Our method detected as little as 2 picograms of protein in as few as 4 nanoliters of material over a 3-log dynamic range. We quantified MYC and BCL2 oncoproteins as well as changes in cancer signaling proteins including ERK, MEK, JNK, STAT3/5 and apoptotic proteins such as caspase 3. The requirement of only a small amount of material enabled us to analyze serial samples of the same tumor in vivo, as we demonstrated in mouse models of lymphoma and in human tumor specimens; oncoprotein phosphorylation decreased in patient samples obtained before and after initiating treatment with imatinib or atorvastatin. We have demonstrated that our method has utility both for pre-clinical and clinical studies.

Our method enables the analysis of solid tissue specimens such as from tumor biopsies, as we illustrate through the analysis of lymphoma specimens. Thus we could quantify differences in MYC and BCL2 oncoprotein expression in normal lymph tissue and different non-Hodgkin's lymphoma subtypes, including Burkitt's and Follicular lymphomas. DLBCL and marginal zone lymphomas were not as readily distinguished, underlining that lymphomas can have complex patterns of oncoprotein overexpression and single proteomic measurements are not sufficient to distinguish most subtypes. The pathological diagnosis of lymphoma as well as other tumor subtypes requires the combination of a number of analytical methods including histological, biochemical and genetic techniques. Our approach has unique features that may complement these existing methodologies.

We can precisely measure oncoprotein isoforms that are useful in the analysis of the therapeutic response in clinical tumor specimens. Using our approach, we were able to identify specific and rare ERK isoforms in vivo in patients with CML that would only be detectable with large amounts of tumor tissue for alternate techniques of 2-D blots or mass spectrometry. Charge-based separation via isoelectric focusing of each protein isoform based upon its unique pI allowed simultaneous quantification of multiple isoforms of the same protein in relative proportions that could not have been detected a priori by Western or FACS techniques. Our results would have been missed by conventional immunoassay or flow cytometric (FACS) techniques since commercially available immunoreagents for activated ERK are raised against the dual phospho-ERK epitopes. Unlike FACS, our samples did not require processing into a single cell suspension, fixation or permeabilization. Furthermore, decreased ERK2 phosphorylation correlated with the clinical response to TK inhibitors.

In addition, we were able to serially sample tumors in patients with lymphoma for a biologic response to a therapeutic agent, atorvastatin. Our observations illustrate that NIA can be used to interrogate the protein signature of and identify biomarkers for response to known and novel therapeutic agents.

Our results demonstrate how a nanoscale proteomic technology can be used to uncover unanticipated changes in protein signaling in vivo. Small perturbations in the equilibrium between active and inactive protein isoforms may have dramatic effects on the biologic state of a cell. Our approach provides a new technique that can be incorporated into pre-clinical and clinical studies to evaluate subtle shifts in protein abundance and modification that may be useful for the discovery of new drugs that target protein pathways and the identification of biomarkers of therapeutic efficacy.

Methods

Nano-Fluidic Proteomic Immunoassay (NIA).

The NIA experiments were performed using a Firefly™ or CB1000™ instrument (Cell Biosciences). Briefly, for each capillary analysis, 4 nanoliters of 10 mg/ml lysate were diluted to 0.2 mg/ml in 200 nanoliters HNG-based lysis buffer [20 mM Hepes pH 7.5, 25 mM NaCl, 0.1%, 10% glycerol, Sigma Phosphatase Inhibitor Cocktail 1, Calbiochem Protease Inhibitor] or 200 nanoliters Bicine/CHAPS lysis buffer. 200 nanoliters sample mix containing internal pI standards were added. The Firefly system first performed a charge-based separation (isoelectric focusing) in a 5 cm long, 100 micron inner-diameter capillary. Predicted pI's were calculated using Scansite. Each sample was run on a panel of different pH gradients (3-10, 5-9) to optimize the resolution of different peak patterns. After separation and photo-activated in-capillary immobilization, proteins were detected with antibodies: MYC protein expression was detected using the C-19 rabbit polyclonal antibody that recognizes mouse and human MYC (Santa Cruz Biotechnology). BCL2 protein expression was detected using the clone 124 mouse monoclonal antibody that recognizes human BCL2 (Dako Laboratories). Total ERK1/2 protein expression was detected using a rabbit polyclonal antibody that recognizes mouse and human ERK1/2 (Upstate). Phospho-ERK 1/2 protein expression was detected using a mouse monoclonal antibody that recognizes both mouse and human pERK 1/2 (Cell Signaling). Additional antibodies used were: activated caspase 3 (Cell Signaling), MEK1 (Upstate), pMEK1 (Novus), MEK2 (Abcam), pSTAT3 (Cell Signaling), pSTAT5 (Cell Signaling), pJNK (Cell Signaling), HSP70 (Novus).

NIA Peak Area Quantitation.

Quantitation of the peaks is performed using peak analysis software. The start and end of each peak, and a flat baseline were manually selected. The area of each peak was calculated by dropping verticals to the baseline at the peak start and end, and summing the area between the start and endpoints. NIA has been shown to be able to discriminate between and quantitate phosphorylated and unphosphorylated isoforms of ERK in a single sample, using a total ERK antibody. The areas under different peaks within a single tracing represented various ERK isoforms. To calculate the percentage p-ERK2 peak 3, the area under peak 3 was divided by the sum of the area under the total ERK peaks. Samples were run in duplicate.

NIA Pseudo-Blot Generation.

The pseudo-blots were created by a linear mapping of the signal intensity to a grayscale image. Each pseudo-blot lane is representative of a single capillary and consists of horizontal bands corresponding proportionally to the signal present. Absence of signal is white, while increasing signal is seen as an increasing dark band. It should be noted that what is seen as a single band of protein in a size-based western, can appear as a single band by NIA or multiple bands when multiple charged isomers of the protein are present.

Human Tumor Samples.

Tissues were obtained and banked from patients per Stanford University IRB-approved protocols. Informed consent was obtained from all subjects. Burkitt lymphomas and T-ALL tissues were frozen in OTC blocks. Follicular lymphomas were dissociated into single cell suspension and stored in heat inactivated FBS +10% DMSO in liquid nitrogen. CML and CLL cells were isolated from total blood by ficoll separation, resuspended in heat inactivated FBS +10% DMSO, and stored in liquid nitrogen. Tumor cells stored in liquid nitrogen were thawed at 37° C. into prewarmed PBS and washed once in PBS immediately before use.

Data and Statistical Analysis.

NIA Multipeak fitting and peak area calculations were done with Peak Fit v4.11 (Systat Software), using Gaussian peaks with variable widths, as previously described. To obtain $R^2$ correlation coefficients, the best fit line was calculated by linear regression with IGOR Pro version 5.03 (Wavemetrics). NIA quantitations of MYC and BCL2 were compared to the relative intensity of respective quantified Western Blot bands using Pearson correlation. Paired t-test (two-tailed) was used to analyze percent of p-ERK2 peak 3 before and during treatment. Mann Whitney Rank sum test was performed on the panels of patient specimens using Prism v4.0 (GraphPad). Prism v4.0 (GraphPad) was also used for Fisher's exact test (2 tailed) analysis of contingency table data for MYC and BCL2.

Normalization of NIA Data.

Normalization of NIA data was performed in a similar fashion as traditional western blots or other molecular biology assays. HSP70 was used as a "housekeeping" protein for NIA normalization. Relative luminescent units (RLU) were calculated by dividing the measured peak area for protein of interest by the measured peak area of HSP-70 and expressed as a percentage. Across different experiments, a standardized lysate control was used for calibration of instruments and runs.

Recombinant Proteins.

MYC protein (Active Motif, Carlsbad, Calif.) or BCL2 protein (R&D Systems, Minneapolis, Minn.) were added to lysis buffer.

Tissue Culture.

Tumor derived cell lines were grown in RPMI (GIBCO) media containing 10% FCS, 1% penicillin/streptomycin (GIBCO), and 0.000003% betamercaptoethanol (Sigma). Cells were grown in T25 flasks in incubators maintained at 37 degrees with 5% carbon dioxide.

Imatinib Treatment In Vitro.

100 mg Imatinib (Novartis, Basel, Switzerland) tablets were dissolved in sterile PBS at 37° C. and added to media for a final concentration of 10 mM in vitro.

Conditional Oncogene Expression.

All experiments were performed with the approval from the Stanford University Administrative Panel on Laboratory Animal Care. The TRE-MYC transgenic line generated for these experiments was described previously. The TRE-BCL2 transgenic lines generated for these experiments were generated in conjunction with R. Padua. The Eμ-tTA transgenic line was kindly provided by H. Bujard$_2$. Mice were mated and screened by PCR. Tumor derived cell lines were generated. Syngeneic mice were injected subcutaneously with lymphoma-derived cell lines containing tetregulatable MYC or BCL2. When tumors reached >1 cm$_3$, oncogene expression was suppressed in vivo by injecting mice with 100 μg of doxycycline in PBS IP and adding doxycycline (100 μg/ml) to the drinking water. In vitro, MYC or BCL2 oncogenes were inactivated in tumor derived cell lines by the addition of doxycycline (0.01, 0.05, 2, or 20 ng/ml, final concentration) to the media.

Tumor Sampling of Transgenic Tumors by Fine Needle Aspiration (FNA).

We performed serial fine needle aspiration procedures (FNAs) on mice to obtain cell samples from subcutaneous lymphoma tumors before and three days after oncogene inactivation. Continuous negative pressure was applied to a 2 ml syringe with 20 gauge needle while 10 passes were made through the subcutaneous tumor. Specimens were collected into PBS. Red blood cells were removed using Pharmalyse (BD). Each FNA procedure obtained an average of 7 million cells.

Western.

Western analysis was performed using conventional techniques. Lymphoid tissues were disrupted and protein was isolated in HNTG lysis buffer [20 mM Hepes pH 7.5, 25 mM NaCl, 0.1%, 0.1% Triton X-100, 10% glycerol, Sigma Phosphatase Inhibitor Cocktail 1, Calbiochem Protease Inhibitor], then sonicated for 30 seconds, 5 minutes on ice (repeated twice). CML cells and CML patient specimens were lysed in RIPA lysis buffer RIPA lysis buffer [25 mM Hepes pH 7.5, 150 mM NaCl, 1% NP 40, 0.25% Na-deoxycholate, 10% glycerol, Sigma Phosphatase Inhibitor Cocktail 1, Calbiochem Protease Inhibitor]. 50 ug protein was loaded in each lane, as quantitated by the Bicinchoninic Acid Protein Assay (Pierce). Proteins were electrophoresed on 10% Tris-HCl polyacrylamide gels at 100 V for 60 min and transferred on PVDF membranes at 100 V for 60 min. The membrane was blocked in 5% nonfat dry milk solution in TBS at 4-8° C. overnight. Blots were incubated with primary antibodies at 4-8° C. overnight. MYC, BCL2, ERK, p-ERK, activated caspase 3, pMEK1, pMEK1, pSTAT5, pJNK and HSP70 were detected with the same primary antibodies used for NIA. Blots were washed three times with TBST and then incubated for one hour with secondary anti-mouse or anti-rabbit HRP-conjugated antibodies (Amersham). ECL detection kit (Amersham) was used for antibody detection. The western data was quantitated using Image Quant and Data Acquisition & Analysis Version 7.3 software (Van Mierlo).

Phospho-Protein FACs.

Cells were fixed in 1.6% paraformaldehyde at 37° C. for 10 minutes, permeabilized with 100% methanol for 10 minutes at room temperature, then washed with PBS, centrifuged at 2000 RPM for 5 minutes, subsequently washed with PBS 1% BSA, then resuspended in 50 ul of PBS 1% BSA. 1 million cells per FACs tube were stained with 10 ul anti-Phospho-ERK1/2 (Thr202/Tyr204):PE (BD Biosciences Pharmingen) in 100 ul PBS 1% BSA. After a 30 minute incubation in the dark, samples were washed once with PBS 1% BSA and subsequently analyzed using a benchtop FACSCAN (Becton-Dickinson) flow cytometer. 10,000 ungated events were collected per sample.

O'Neill, R. A., et al. Isoelectric focusing technology quantifies protein signaling in 25 cells. *Proc Natl Acad Sci USA* 103, 16153-16158 (2006)

Felsher, D. W. & Bishop, J. M. Reversible tumorigenesis by MYC in hematopoietic lineages. *Mol Cell* 4, 199-207 (1999).

Kistner, A., et al. Doxycycline-mediated quantitative and tissue-specific control of gene expression in transgenic mice. *Proc Natl Acad Sci USA* 93, 10933-10938 (1996).

Towbin, H., Staehelin, T. & Gordon, J. Electrophoretic Transfer of Proteins from Polyacrylamide Gels to Nitrocellulose Sheets: Procedure and Some Applications. *PNAS* 76, 4350-4354 (1979).

O'Neill, R. A., et al. Isoelectric focusing technology quantifies protein signaling in 25 cells. *Proc Natl Acad Sci USA* 103, 16153-16158 (2006).

Example 2

Nanoscale Quantification of Phosphorylated and Unphosphorylated ERK and MEK Isoforms Differentiates Tumor and Non-Tumor Clinical Specimens We have developed the use of a highly sensitive microfluidic nano-immunoassay system (NIA) to perform detailed analysis of ERK and MEK activation in hematopoietic and solid tumors. We described above the use of NIA for measurement of proteins in as little as 4 nL of lysate from lymphoma and leukemia specimens. Now, we present results measuring specific isoforms of MAPK proteins in fine needle aspirates (FNAs) from patients with solid tumors and in blood buffy coats from patients with Myelo-Dysplastic Syndrome (MDS).

Using a single antibody that recognizes both the phosphorylated and unphosphorylated isoforms of ERK, we can determine levels of each ERK isoform, and also percent phosphorylation of ERK. NIA revealed that different tumor types could be distinguished based upon differing patterns of ERK isoforms. To determine if NIA can measure signaling changes during treatment with novel drugs, human leukemic cells were treated with a PLK-1 inhibitor, ON01910 (Onconova, Inc). Surprisingly, only 5% of ERK was phosphorylated in the TF1 cell line, whereas 90% of MEK was phosphorylated. MEK2 phosphorylation decreased by 20% after ON01910 treatment. Our studies demonstrate NIA can be used to identify specific changes in the MAPK pathway that distinguish normal from malignant cells and quantify response of cells to a targeted therapeutic.

We determined optimal conditions for handling and processing of human solid tumor FNA and blood buffy coat specimens for NIA proteomic analysis; used NIA to measure phosphorylation and percent phosphorylation of MAPK proteins in clinical samples; determined if phosphorylation and percent phosphorylation of MAPK proteins change upon targeted treatment; and evaluated proteomic response to novel therapies in cells sampled from patients at different time points during treatment.

We found that NIA measurements are stable in specimens kept on ice up to 60 minutes. Wth representative MEK measurements for FNA of solid tumor kept on ice for 0, 30, 60 minutes, statistical analysis indicated no significant difference between groups, corrected for multiple testing. See FIG. 14.

In particular, although AKT has been reported to be unstable, it was found that some AKT isoforms are stable for over 30 minutes and even 60 minutes on ice. Therefore, optimal sample handling may include transport on ice. Removal of blood from a clinical sample can cause variability of measurements, so desirable handling protocols do not remove blood. It was found that NIA measurements were the same in freshly lysed and frozen samples.

Figure 15B:
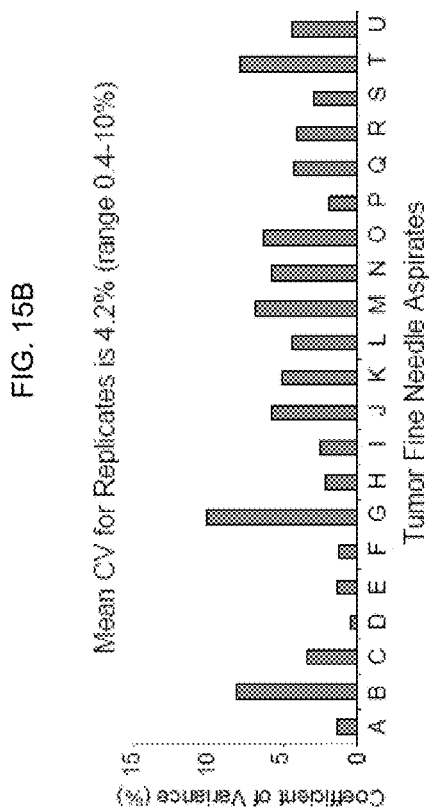
FIG. 15A-15B. FNAs from 20 tumors were analyzed using NIA to measure percent ERK phosphorylation. Samples were run in triplicate.
Figure 15A:
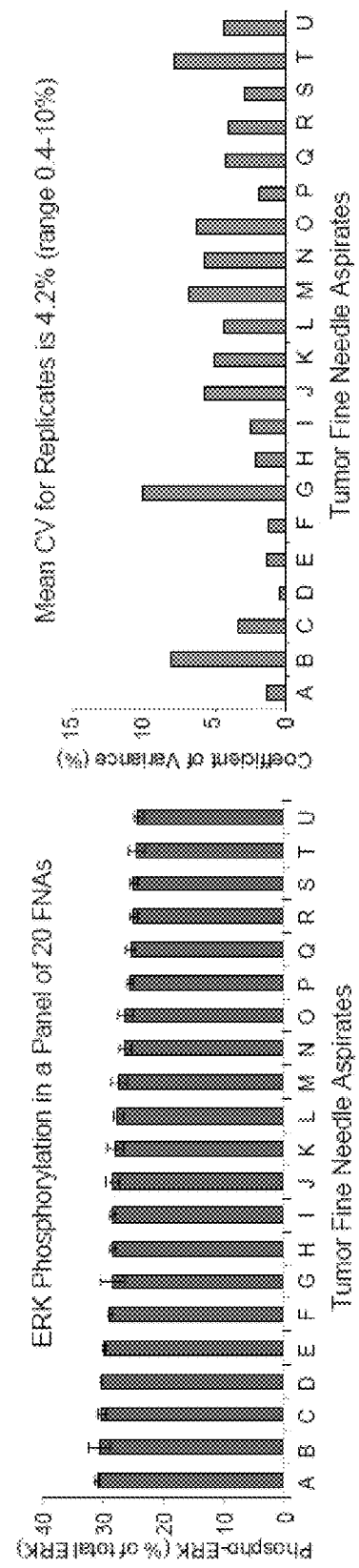

The NIA results were validated with a mean coefficient of variance less than 5%, and the protocols were validated across 19 different tumor types, including sarcoma, angiomyolipoma; dysgerminoma, testicular, melanoma, uterine, ovary, bladder, kidney, thyroid, adenoid cystic, neuroendocrine, thymus, adenocarcinoma, lung, colon, pancreas, stomach, squamous cell carcinoma, and head and neck. See FIG. 15.

ERK was found to be more highly phosphorylated in solid tumors than in lymphomas, using NIA measurements of percent ERK phosphorylation in solid tumor and lymphoma clinical specimens. Phosphorylated ERK distinguishes tumor from non-tumor tissue, using NIA measurements of ERK in tumor (T) and non-tumor (N) clinical specimens. NIA analysis reveals increased phosphorylation of ERK in some paired patient tumor and non-tumor samples, decreased phosphorylation in others. NIA analysis also revealed differential phosphorylation of ERK and MEK in MDS and control patients.

Treatment with ON01910 altered phosphorylation of signaling proteins in TF1 cells. Using NIA measurements of phosphorylated JNK and MEK2 in TF1 cells before and after treatment with ON01910, NIA analysis reveals increased phosphorylation of JNK and decreased phosphorylation of MEK2 in the human leukemic cell line TF1 after 24 hr of treatment with ON01910.

Phosphorylation of STAT3/5 decreased in lymphoma patients treated with atorvastatin. Tumor cells were sampled from lymphoma patients day 1 and day 8 of atorvastatin treatment. Both NIA and FACS analysis demonstrate that CD20 positive cells from patients with lymphoma show a dramatic decrease in STAT3 and STAT5 phosphorylation.

A 23-parameter protein profile was developed in solid tumors. The 23 parameters were:

| ERK Normalized Values: | ERK Relative Ratios: |
|---|---|
| Total ERK1/2 | % phospho-ERK1/2 |
| Phospho-ERK1/2 | % Unphosphorylated ERK1/2 |
| Unphosphorylated ERK1/2 | % Phospho-ERK1 |
| Total ERK1 | % Unphosphorylated ERK1 |
| Phospho-ERK1 | % Phospho-ERK2 |
| pERK1 | % Unphosphorylated ERK2 |
| ppERK1 | % pERK1 |
| Unphosphorylated ERK1 | % ppERK1 |
| Total ERK2 | % pERK2 |
| Phospho-ERK2 | % ppERK2 |
| pERK2 | |
| ppERK2 | |
| Unphosphorylated ERK2 | |

The percent of phosphor-ERK is a particularly useful marker for kidney cancer. Each bar is a ratio of: the value of % phospho-ERK for the non-tumor kidney specimen DIVIDED by the value of the % phospho-ERK for the paired kidney tumor specimen. The Y-axis of the graph is on a log scale.

The percent of ppERK1 is a particularly selective marker for head and neck cancer.

NIA can be used to assess changes in total and phosphorylated protein isoforms during therapeutic interventions in hematopoietic disorders and solid tumors. FACS and NIA together allow measuring when proteomic effects are specific to tumor cells and if novel agents preferentially modulate specific isoforms of signaling proteins.

Methods

Protocol for NIA analysis of Solid Tumor Fine Needle Aspirate (FNA). Cytopathologist performs at least 10 passes through tissue and collects FNA into 4 mL RPMI. Put FNA suspension on ice for transport and stores at 4 C for pick up by lab. Minimize time between collection by cytopathologist and snap freezing FNA pellets. Divide FNA suspension in to 1.5 mL tubes. Equally distribute suspension between 3 tubes. Spin 1.5 mL tubes at 5000 rpm for 5 min at 4 C. Remove RPMI with P1000 filter tip very carefully and avoid pellet as much as possible. Expect 1-2 µL max residual supernatant volume. Snap freeze pellets in liquid N2. Store at −80 C until ready for lysis. When lyse pellet, thaw on ice 1-2 min. Make up MPER lysis buffer with following inhibitors: a. Aqueous Protease Inhibitor (Cell Biosciences, 25×); b. Sigma Phosphatase Inhibitor (use 1:100); c. Calbiochem Protease Inhibitor (use 1:500). Add 20 µL lysis buffer to pellet approximately equivalent in size to 1 million cells. Completely resuspend cells in lysis buffer by pipetting up and down (can do a quick, low speed vortex). Leave on ice 30 min. Spin tube at max speed (14K rpm) for 10 min at 4 C. Remove supernatant with P200 filter tip. This is the lysate. Determine protein concentration of lysate using Pierce BCA kit. Optional step: Aliquot and snap freeze in liquid N2. Store −80 C. Calculate volume of lysate needed for final protein concentration of 0.1 mg/mL per well.

Load 20 µL primary antibodies per well and 30 µL secondary antibodies per well in to 384-well plate and keep plate on ice at all times. Make up luminol and load 30 µL per well in to plate. Make up Sample Diluent [MPER with DMSO Inhibitor Mix (50×)] and keep on ice. Aliquot 6 µL premix per well to 0.5 mL tubes. Then add appropriate volume of Sample Diluent to tubes with premix. Add appropriate volume of lysate to tubes with premix and Sample Diluent. Volume of Sample Diluent plus lysate is equal to 6 µL per well. Pipet up and down 20×, vortex at medium setting briefly for 7 seconds, then pipet up and down 30×. Load 10 µL of premix/lysate per well. Spin plate 1000 rpm 10 sec to remove bubbles in wells.

Antibodies include ERK1/2 Millipore, 06-182 1:300 Goat anti-Rabbit, 1:500; HSP70 Novus Biologicals, 600-571 1:5000 Goat anti-Mouse, 1:250; MEK1 Upstate, 07-641 1:100 Goat anti-Rabbit, 1:100; MEK2 Cell Signaling, 9125 1:100 Goat anti-Rabbit, 1:100; pSTAT5 Upstate, 06-867 1:100 Goat anti-Rabbit, 1:100; pSTAT3 Abcam, AB30646 1:50 Goat anti-Rabbit, 1:100; AKT Santa Cruz, SC8312 1:50 Goat anti-Rabbit, 1:100.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for serial monitoring of specific changes in protein isoforms in clinical tumor microbiopsy specimens, the method comprising;
    performing nanofluidic proteomic immunoassay (NIA) on a tumor microbiopsy cellular sample from an individual for simultaneous quantification of multiple isoforms of a single protein, wherein said cellular sample is maintained on ice for greater than 30 mins prior to cell lysis;
    determining the ratio of isoforms of the protein in said cellular sample;
    comparing the ratio of isoforms in said cellular sample with a paired sample from said individual, wherein the paired sample from said individual comprises two samples taken from the same tumor at different time points; and
    identifying from the comparison of isoform ratios in said paired samples a determination of specific changes in protein isoforms, as measured by isoelectric focusing.

2. The method of claim 1, wherein the microbiopsy cellular sample is less than 100,000 cells.

3. The method of claim 1, wherein the protein is an oncoprotein.

4. The method of claim 3, wherein the isoform differs from alternative isoforms of the same oncoprotein by total level of phosphorylation or percent phosphorylation relative to the paired sample.

5. The method of claim 4, wherein the oncoprotein is ERK2.

6. The method of claim 1, wherein multiple time points from a single tumor in response to treatment are compared.

7. The method of claim 1, wherein the cellular sample was previously frozen.

8. The method of claim 1, wherein said cellular sample comprises blood cells.

9. The method of claim 1, wherein said microbiopsy cellular sample comprises kidney cancer cells.

10. The method of claim 1, wherein said microbiopsy cellular sample comprises head and neck cancer cells.

11. The method of claim 1, wherein the microbiopsy cellular sample is less than 1000 cells.

12. The method of claim 1, wherein two or more oncoproteins are analyzed, and the two or more oncoproteins are selected from pSTAT3, pSTAT5, myc, bcl2, MEK1, MEK2, pJNK, akt isoforms, total ERK1/2, phospho-ERK1/2, unphosphorylated ERK1/2, total ERK1, pERK1, ppERK1, unphosphorylated ERK1, total ERK2, pERK2, ppERK2, unphosphorylated ERK2; and ERK relative ratios for: % phospho-ERK1/2, % unphosphorylated ERK1/2, % phospho-ERK1, % unphosphorylated ERK1, % phospho-ERK2, % unphosphorylated ERK2, % pERK1, % ppERK1, % pERK2, % ppERK2, % phospho-MEK1 and % phospho-MEK2.

13. A method for serial monitoring of specific changes in protein isoforms in clinical tumor microbiopsy specimens, the method comprising;
    performing nanofluidic proteomic immunoassay (NIA) on a tumor microbiopsy cellular sample of less than 100 cells from an individual for simultaneous quantification of multiple isoforms of a single protein, wherein said cellular sample is maintained on ice for greater than 30 minutes prior to cell lysis;
    determining the ratio of isoforms of the protein in said cellular sample;
    comparing the ratio of isoforms in said cellular sample with a paired sample from said individual, wherein the paired sample from said individual comprises two samples taken from the same tumor at different time points; and
    identifying from the comparison of isoform ratios in said paired samples a determination of specific changes in protein isoforms, as measured by isoelectric focusing.

14. The method of claim 1 or 13, wherein said cellular sample is obtained by fine needle aspiration (FNA).

15. A method for serial monitoring of specific changes in ERK2 protein isoforms in clinical CML microbiopsy specimens or blood samples to determine response to a tyrosine kinase inhibitor, the method comprising;
    performing nanofluidic proteomic immunoassay (NIA) on a clinical CML microbiopsy specimen or blood sample from an individual for simultaneous quantification of multiple isoforms of a single protein wherein said cellular sample is maintained on ice for greater than 30 mins prior to cell lysis;
    determining the ratio of isoforms of the protein in said clinical CML microbiopsy specimen or blood sample; and comparing the ratio of isoforms in said clinical CML microbiopsy specimen or blood sample with a paired sample from said individual, wherein the paired sample from said individual comprises two samples taken at different time; and identifying from the comparison of isoform ratios in said paired samples a determination of specific changes in protein isoforms, as measured by isoelectric focusing, wherein the percentage of the single phosphorylated form is down regulated in a clinical CML microbiopsy specimen or blood sample from a patient that is responsive to the tyrosine kinase inhibitor.

16. The method of claim 15, wherein the tyrosine kinase inhibitor is imatinib.

* * * * *

UNITED STATES PATENT AND TRADEMARK OFFICE
CERTIFICATE OF CORRECTION

PATENT NO. : 10,145,851 B2
APPLICATION NO. : 15/004601
DATED : December 4, 2018
INVENTOR(S) : Felsher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 248 days.

Signed and Sealed this
Tenth Day of December, 2019

Andrei Iancu
*Director of the United States Patent and Trademark Office*